US012806177B2

(12) United States Patent
Kunzelmann

(10) Patent No.: US 12,806,177 B2
(45) Date of Patent: Nov. 24, 2026

(54) COMPOUND FOR USE IN THE TREATMENT OF A DISEASE CHARACTERIZED BY DYSREGULATED MUCUS PRODUCTION AND/OR SECRETION

(71) Applicant: UNIVERSITÄT REGENSBURG, Regensburg (DE)

(72) Inventor: Karl Kunzelmann, Regensburg (DE)

(73) Assignee: UNIVERSITÄT REGENSBURG, Regensburg (DE)

( * ) Notice: Subject to any disclaimer, the term of this patent is extended or adjusted under 35 U.S.C. 154(b) by 198 days.

(21) Appl. No.: 17/285,031

(22) PCT Filed: Oct. 10, 2019

(86) PCT No.: PCT/EP2019/077433
§ 371 (c)(1),
(2) Date: Apr. 13, 2021

(87) PCT Pub. No.: WO2020/078813
PCT Pub. Date: Apr. 23, 2020

(65) Prior Publication Data

US 2021/0283110 A1 Sep. 16, 2021

(30) Foreign Application Priority Data

Oct. 15, 2018 (EP) .................................... 18200399

(51) Int. Cl.
*A61K 31/426* (2006.01)
*A61K 31/122* (2006.01)
*A61K 31/167* (2006.01)
*A61K 31/343* (2006.01)

(52) U.S. Cl.
CPC .......... *A61K 31/426* (2013.01); *A61K 31/122* (2013.01); *A61K 31/167* (2013.01); *A61K 31/343* (2013.01)

(58) Field of Classification Search
CPC .. A61K 31/426; A61K 31/122; A61K 31/167; A61K 31/343; A61L 31/426
See application file for complete search history.

(56) References Cited

U.S. PATENT DOCUMENTS

| | | | | |
|---|---|---|---|---|
| 2002/0115716 A1* | 8/2002 | Chaturvedi | A61P 43/00 514/529 |
| 2006/0160867 A1 | 7/2006 | Freedman | |
| 2017/0056347 A1 | 3/2017 | Glick et al. | |
| 2017/0290812 A1* | 10/2017 | Darteil | A61P 9/10 |

FOREIGN PATENT DOCUMENTS

| | | | | |
|---|---|---|---|---|
| WO | WO-2004098510 A2 * | 11/2004 | A61K 31/198 |
| WO | WO-2009023509 A2 * | 2/2009 | A61K 31/137 |
| WO | 2018/026441 A1 | 2/2018 | |
| WO | WO-2018148113 A1 * | 8/2018 | C07C 215/42 |

OTHER PUBLICATIONS

Miner et al., "The Anthelminthic Niclosamide and related compounds represent potent TMEM16A antagonists that fully relax mouse and human airway rings", C26 Asthma in Infants and Children / Poster Discussion Session / May 23, 2017/9:15 AM-11:15 AM / Room 201 Walter E. Washington Convention (Year: 2017).*
Hiemstra et al., "The Innate Immune Function of airway epithelial cells in inflammatory lung disease", Eur Respir J 2015; 45: pp. 1150-1162, published online Feb. 19, 2015 (Year: 2015).*
"Bronchodilators", Cystic Fibrosis News Today, Oct. 4, 2017, Retrieved from the web: <cysticfibrosisnewstoday.com/bronchodilators/ > (Year: 2017).*
Hemphill et al., "Nitazoxanide, a broad-spectrum thiazolide anti-infective agent for the treatment of gastrointestinal infections", Taylor and Francis Online, Apr. 24, 2006 (Year: 2006).*
Mccauly et al., "Three cheers for the goblet cell: maintaining homeostasis in mucosal epithelia", HAL open Science, Jan. 5, 2017 (Year: 2017).*
Diag et al., "Increased interleukin 8 Expression in the colon mucosa of patients with inflammatory Bowel Disease", Gut, 1996, pp. 216-222 (Year: 1996).*
Xiao-Qing Ji et al., "Pulmonary Manifestations of inflammatory bowel disease", World J Gastroenterol, Oct. 7, 2014, vol. 20, issue 37 (Year: 2014).*
Collin et al., "Loss of ciliated cells and altered airway epithelial integrity in cystic fibrosis", Journal of Cystic Fibrosis, vol. 20, Issue 6, Nov. 2021 (Year: 2021).*
Cantin et al., "Inflammation in cystic fibrosis lung disease: Pathogenesis and therapy", J Cyst Fibros. Jul. 14, 2015 (Year: 2015).*
Loo et al., Corrector-mediated rescue of misprocessed CFTR mutants can be reduced by the P-glycoprotein drug pump, Biochemical Pharmacology, Feb. 1, 2012 (Year: 2012).*
Wang et al., Correctors Promote Maturation of Cystic Fibrosis Transmembrane Conductance Regulator (CFTR)-processing Mutants By Binding to the Protein, Journal of Biological Chemistry, Sep. 21, 2007 (Year: 2007).*
Eidelwein, Alexandra et al. (Oct. 2009) "Nitazoxanide to Treat Exacerbations of Pediatric Inflammatory Bowel Disease (IBD)", American Journal of Gastroenterology, vol. 104, No. Suppl. 3, p. S545, Abstract.
Huang, Fen et al. (Oct. 2, 2012) "Calcium-activated chloride channel TMEM16A modulates mucin secretion and airway smooth muscle contraction," PNAS, vol. 109, No. 40, pp. 6354-16359.
Lin, Jiachen et al. (Mar. 10, 2015) "TMEM16A mediates the hypersecretion of mucus induced by Interleukin-13," Experimental Cell Research, vol. 334, No. 2, pp. 260-269.
Lin, Meng-Juan et al. (Aug. 29, 2018) "Colonic Hypermotility in a Rat Model of Irritable Bowel Syndrome is Associated with Upregulation of TMEM16A in Myenteric Plexus," Digestive Diseases and Sciences, vol. 63, No. 12, pp. 3329-3338.

(Continued)

*Primary Examiner* — Andrew D Kosar
*Assistant Examiner* — Gillian A Hutter
(74) *Attorney, Agent, or Firm* — SALIWANCHIK, LLOYD & EISENSCHENK

(57) ABSTRACT

The present invention relates to a compound for use in a method of treating a disease selected from cystic fibrosis, ulcerative colitis, and irritable bowel syndrome, wherein said compound is an inhibitor of a TMEM16 protein, preferably of TMEM16A and/or TMEM16F.

7 Claims, 20 Drawing Sheets

(56) References Cited

OTHER PUBLICATIONS

Namkung, Wan et al. (Jan. 21, 2011) "TMEM16A Inhibitors Reveal TMEM16A as a Minor Component of Calcium-activated Chloride Channel Conductance in Airway and Intestinal Epithelial Cells," Journal of Biological Chemistry, vol. 286, No. 3, pp. 2365-2374.
Seo, Yohan et al. (Jul. 21, 2015) "Inhibition of ANO1/TMEM16A Chloride Channel by Idebenone and Its Cytotoxicity to Cancer Cell Lines," Plos One, vol. 10, No. 7, pp. 1-15.
Suppy, William (Oct. 2009) "Nitazoxanide for the Treatment of Blastocystis hominis in Patients with Irritable Bowel Syndrome," American Journal of Gastroenterology, vol. 104, Suppl 3, p. S493, Abstract.

* cited by examiner

A

B

A

B

COMPOUND FOR USE IN THE TREATMENT OF A DISEASE CHARACTERIZED BY DYSREGULATED MUCUS PRODUCTION AND/OR SECRETION

CROSS REFERENCE TO RELATED APPLICATIONS

This application is a National Stage Application of International Application Number PCT/EP2019/077433, filed Oct. 10, 2019; which claims priority to European Patent Application No. 18 200 399.6, filed Oct. 15, 2018.

FIELD OF THE INVENTION

The present invention relates to a compound for use in a method of treating a disease selected from cystic fibrosis, ulcerative colitis, and irritable bowel syndrome, wherein said compound is an inhibitor of a TMEM16 protein, preferably of TMEM16A and/or TMEM16F.

BACKGROUND OF THE INVENTION

Excessive mucus production and/or secretion are pathological dysfunctions which play a role in many diseases. For example, excessive airway mucus plays a role in diseases such as cystic fibrosis (CF), ulcerative colitis, and irritable bowel syndrome. Excessive intestinal mucus plays a role in diseases such as CF, ulcerative colitis, and irritable bowel syndrome. Regeneration of the physiological balance of mucus secretion and/or mucus production, ideally combined with relaxation of the airways, is a promising causal approach for treating diseases characterized by dysregulated mucus secretion and/or mucus production, which are typically accompanied by inflammation. Thus, there is a demand for compounds capable of controlling excessive mucus secretion and/or production. The present inventors disclose compounds, such as inhibitors of TMEM16A and other TMEM16 proteins including TMEM16F, for use in a method of treating a disease selected from cystic fibrosis, ulcerative colitis, and irritable bowel syndrome. These compounds act by reducing basal mucus secretion that is activated by constitutive release of the purinergic agonist ATP. The compounds also indirectly inhibit cholinergic mucus release by antagonizing mucus production.

In healthy lungs mucus is formed by secretion and hydration of gel forming mucins from goblet cells and club cells (also referred to as Clara cells) producing MUC5AC and MUC5B, and from submucosal glands releasing MUC5B. The major mucin released by goblet cells in the gastrointestinal tract is MUC2.

Although clear differences exist between airway and intestinal goblet cells, they share common features such as low pH and high $Ca^{2+}$ content in their secretory granules. Despite protective functions of mucus in a physiological state, mucus becomes a severe problem when hypersecreted upon mucous cell metaplasia during inflammatory lung diseases such as CF and/or during gastrointestinal medical conditions such as ulcerative colitis and irritable bowel syndrome. Mucus hyperproduction causes airway obstruction, reduced mucociliary clearance and chronic inflammatory lung disease, the predominant problems in CF. In CF, mucus is particularly viscous and adhesive due to compromised $Cl^-$ and $HCO_3^-$ secretion caused by defective cystic fibrosis transmembrane conductance regulator (CFTR) channels. Furthermore, dysregulated mucus secretion and/or production also play a role in diseases such as ulcerative colitis and irritable bowel syndrome. There is a need for effective means to treat diseases characterized by dysregulated mucus secretion and/or mucus production.

TMEM16A is a $Ca^{2+}$ activated chloride channel in the airways and the intestine and has been associated with goblet cell metaplasia. Expression of TMEM16A is strongly upregulated in CF, and co-occurs with mucus hypersecretion. TMEM16F has been proposed to be essential for $Ca^{2+}$ dependent scramblase activity.

Huang et al. [1] shows that expression of the $Ca^{2+}$ activated $Cl^-$ channel TMEM16A (anoctamin 1) is strongly upregulated in CF and asthma, which co-occurs with goblet cell metaplasia and mucus hypersecretion. Furthermore, Huang et al. discloses expression of TMEM16A in mucus producing cells and to a lesser degree in ciliated epithelial cells [1].

Lin et al. [2] discloses that TMEM16A overexpression stimulates mucus production and TMEM16A knockout inhibits mucus production.

Miner et al. [3] discloses that niclosamide and nitazoxanide are inhibitors of TMEM16A.

The present invention aims at providing a compound for use in the treatment of a disease characterized by dysregulated mucus secretion and/or production. Furthermore, the aim of the present invention is providing a compound for use in a method of treating a disease selected from cystic fibrosis, ulcerative colitis, and irritable bowel syndrome, wherein said compound is an inhibitor of a TMEM16 protein, preferably of TMEM16A and/or TMEM16F.

SUMMARY OF THE INVENTION

The present inventors provide a compound for use in a method of treating a disease characterized by dysregulated mucus secretion and/or mucus production such as cystic fibrosis, ulcerative colitis, and irritable bowel syndrome, comprising inhibiting basal, i.e. ATP-induced mucus secretion and/or mucus production by mucus producing cells.

The present invention discloses that a compound, such as niclosamide, for use according to the present invention has unexpected positive effects on pathophysiological airways and/or gastrointestinal tract, namely by inhibiting mucus secretion, inhibiting mucus production, promoting bronchorelaxation, and having an anti-inflammatory effect.

The present invention discloses a compound for use in a method of treating a disease characterized by dysregulated mucus secretion and/or mucus production, wherein said compound inhibits basal, i.e. ATP-induced mucus secretion, and may inhibit cholinergic mucus secretion indirectly by inhibiting mucus production by mucus producing cells.

The present inventors further disclose that TMEM16A has an essential role for cellular exocytosis, and that this function is not limited to mucus release, but may also control the release of inflammatory mediators.

In a further aspect, the present inventors disclose that inhibiting a TMEM16 protein, such as TMEM16A, does not only inhibit mucus secretion in mucus producing cells in the airways, but also mucus secretion in intestinal mucus producing cells. The present inventors also disclose that inhibiting TMEM16F results in reduced mucus production. Furthermore, the present invention discloses that inhibiting TMEM16 proteins, such as TMEM16A and TMEM16F, inhibit both mucus secretion and mucus production.

In the following, the elements of the invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine two or more of the explicitly described embodiments or which combine the one or more of the explicitly described embodiments with any number of the disclosed and/or preferred elements. Furthermore, any permutations and combinations of all described elements in this application should be considered disclosed by the description of the present application unless the context indicates otherwise.

The present invention relates to a compound for use in a method of treating a disease selected from cystic fibrosis, ulcerative colitis, and irritable bowel syndrome, wherein said compound is an inhibitor of a TMEM16 protein, preferably of TMEM16A and/or TMEM16F, and wherein said compound is selected from a structure of Formula I:

(Formula I)

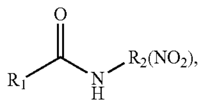

wherein $R_1$ is selected from the group consisting of substituted or unsubstituted aryl or heteroaryl, preferably substituted with one or more substituents selected from the group consisting of halogen, hydroxyl, amino, nitro, cyano, thiol, sulfonyl, carbonyl, carboxyl, alkyl, alkoxy, acetoxy, alkenyl, cycloalkyl, aryl, and heteroaryl, wherein it is preferably substituted or unsubstituted phenyl, more preferably phenyl substituted with one or more substituents selected from hydroxyl, halogen, and acetoxy, wherein $R_2$ is selected from the group consisting of substituted or unsubstituted aryl or heteroaryl, preferably substituted with one or more substituents selected from the group consisting of halogen, hydroxyl, amino, nitro, cyano, thiol, sulfonyl, carbonyl, carboxyl, alkyl, alkoxy, acetoxy, alkenyl, cycloalkyl, aryl, and heteroaryl, wherein it is preferably selected from thiazolyl and phenyl, more preferably thiazolyl and phenyl substituted with halogen, or a pharmaceutically acceptable salt thereof, or wherein said compound is idebenone or benzbromarone, or a pharmaceutically acceptable salt thereof.

In one embodiment, said compound has a structure of Formula II:

(Formula II)

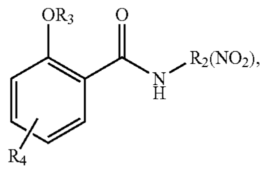

wherein $R_2$ is selected from the group consisting of substituted or unsubstituted aryl or heteroaryl, preferably substituted with one or more substituents selected from the group consisting of halogen, hydroxyl, amino, nitro, cyano, thiol, sulfonyl, carbonyl, carboxyl, alkyl, alkoxy, acetoxy, alkenyl, cycloalkyl, aryl, and heteroaryl, wherein it is preferably selected from thiazolyl and phenyl, more preferably thiazolyl and phenyl substituted with halogen, wherein $R_3$ is selected from the group consisting of hydrogen, substituted or unsubstituted alkyl, particularly acetyl, substituted or unsubstituted alkenyl, substituted or unsubstituted alkinyl, substituted or unsubstituted aryl, substituted or unsubstituted heteroaryl, substituted or unsubstituted cycloalkyl, substituted or unsubstituted heterocycloalkyl, wherein $R_4$ is selected from the group consisting of hydrogen, halogen, hydroxyl, amino, nitro, cyano, thiol, sulfonyl, carbonyl, carboxyl, substituted or unsubstituted alkyl, alkoxy, acetoxy, substituted or unsubstituted alkenyl, substituted or unsubstituted cycloalkyl, substituted or unsubstituted aryl, and substituted or unsubstituted heteroaryl, wherein $R_4$ is preferably halogen and a para-substitution to $OR_3$, or a pharmaceutically acceptable salt thereof, or wherein said compound is idebenone or benzbromarone, or a pharmaceutically acceptable salt thereof.

In one embodiment, said compound has a structure of Formula III:

(Formula III)

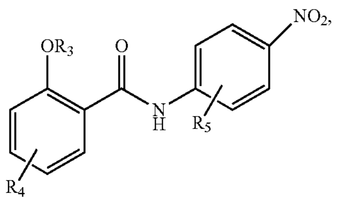

wherein $R_3$ is selected from the group consisting of hydrogen, substituted or unsubstituted alkyl, particularly acetyl, substituted or unsubstituted alkenyl, substituted or unsubstituted alkinyl, substituted or unsubstituted aryl, substituted or unsubstituted heteroaryl, substituted or unsubstituted cycloalkyl, substituted or unsubstituted heterocycloalkyl, wherein $R_4$ is selected from the group consisting of hydrogen, halogen, hydroxyl, amino, nitro, cyano, thiol, sulfonyl, carbonyl, carboxyl, substituted or unsubstituted alkyl, alkoxy, acetoxy, substituted or unsubstituted alkenyl, substituted or unsubstituted cycloalkyl, substituted or unsubstituted aryl, and substituted or unsubstituted heteroaryl, wherein $R_4$ is preferably halogen and a para-substitution to $OR_3$, wherein $R_5$ is selected from the group consisting of hydrogen, halogen, hydroxyl, amino, nitro, cyano, thiol, sulfonyl, carbonyl, carboxyl, substituted or unsubstituted alkyl, alkoxy, acetoxy, substituted or unsubstituted alkenyl, substituted or unsubstituted cycloalkyl, substituted or unsubstituted aryl, and substituted or unsubstituted heteroaryl, or a pharmaceutically acceptable salt thereof, or wherein said compound is idebenone or benzbromarone, or a pharmaceutically acceptable salt thereof.

In one embodiment, said compound has a structure of Formula IV:

(Formula IV)

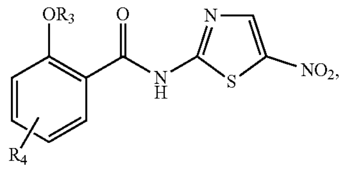

wherein $R_3$ is selected from the group consisting of hydrogen, substituted or unsubstituted alkyl, particularly acetyl, substituted or unsubstituted alkenyl, substituted or unsubstituted alkinyl, substituted or unsubstituted aryl, substituted or unsubstituted heteroaryl, substituted or unsubstituted cycloalkyl, substituted or unsubstituted heterocycloalkyl, wherein $R_4$ is selected from the group consisting of hydrogen, halogen, hydroxyl, amino, nitro, cyano, thiol, sulfonyl, carbonyl, carboxyl, substituted or unsubstituted alkyl, alkoxy, acetoxy, substituted or unsubstituted alkenyl, substituted or unsubstituted cycloalkyl, substituted or unsubstituted aryl, and substituted or unsubstituted heteroaryl, wherein $R_4$ is preferably halogen and a para-substitution to $OR_3$, or a pharmaceutically acceptable salt thereof, or wherein said compound is idebenone or benzbromarone, or a pharmaceutically acceptable salt thereof.

In one embodiment, said compound is selected from 5-chloro-N-(2-chloro-4-nitrophenyl)-2-hydroxybenzamide, also referred to as niclosamide, 2-aminoethanol; 5-chloro-N-(2-chloro-4-nitrophenyl)-2-hydroxybenzamide, also referred to as clonitralid or niclosamide ethanolamine salt,

[2-[(5-nitro-1,3-thiazol-2-yl)carbamoyl]phenyl]acetate, also referred to as nitazoxanide, 2-hydroxy-N-(5-nitro-1,3-thiazol-2-yl)benzamide, also referred to a tizoxanide, (3,5-dibromo-4-hydroxyphenyl) (2-ethyl-1-benzofuran-3-yl) methanone, also referred to as benzbromarone, and 2-(10-hydroxydecyl)-5,6-dimethoxy-3-methyl-1,4-benzoquinone, also referred to as idebenone.

In one embodiment, said compound is selected from 5-chloro-N-(2-chloro-4-nitrophenyl)-2-hydroxybenzamide, also referred to as niclosamide, and 2-aminoethanol 5-chloro-N-(2-chloro-4-nitrophenyl)-2-hydroxybenzamide, also referred to as clonitralid or niclosamide ethanolamine salt.

In one embodiment, said compound is selected from [2-[(5-nitro-1,3-thiazol-2-yl)carbamoyl]phenyl]acetate, also referred to as nitazoxanide, and 2-hydroxy-N-(5-nitro-1,3-thiazol-2-yl)benzamide, also referred to as tizoxanide.

In one embodiment, said disease is characterized by dysregulated basal mucus secretion and/or dysregulated mucus production and/or dysregulated release of proinflammatory cytokines by any of airway epithelial goblet cells, club cells, and ciliated epithelial cells.

In one embodiment, said method of treating involves inhibiting basal mucus secretion and/or mucus production and/or dysregulated release of proinflammatory cytokines in any of airway epithelial goblet cells, club cells, and ciliated epithelial cells.

In one embodiment, said TMEM16 protein is selected from TMEM16A, TMEM16B, TMEM16C, TMEM16D, TMEM16E, TMEM16F, TMEM16G, TMEM16H, TMEM16J, and TMEM16K, preferably selected from TMEM16A and TMEM16F.

In one embodiment, said disease affects the respiratory tract and/or the gastrointestinal tract.

In one embodiment, said disease is cystic fibrosis.

In one embodiment, said disease is ulcerative colitis or irritable bowel syndrome.

In one embodiment, said compound is administered topically or systemically.

In one embodiment, said compound is administered orally, nasally, mucosally, intrabronchially, intrapulmonarily, intradermally, subcutaneously, intravenously, intramuscularly, intravascularly, intrathecally, intraocularly, intraarticularly, or intranodally, wherein said compound is preferably administered orally, nasally, mucosally, intrabronchially, or intrapulmonarily, more preferably orally or nasally.

DETAILED DESCRIPTION

The term "niclosamide", as used herein, refers to a drug which is commonly used to treat tapeworm infestations. It also referred to as 5-Chlor-N-(2-chlor-4-nitrophenyl)-2-hydroxybenzamid having a formula $C_{13}H_8Cl_2N_2O_4$.

The term "niclosamide-ethanolamin", as used herein, refers to an ethanolamine salt of niclosamide which is an antihelminthic compound.

The term "clonitralid", as used herein, refers to niclosamide-olamine which is a niclosamide ethanolamine salt having a formula $C_{13}H_8Cl_2N_2O_4 \cdot C_2H_7NO$.

The term "nitazoxanide", as used herein, relates to a broad-spectrum antiparasitic and broad-spectrum antiviral drug that is commonly used in the treatment of helminthic, protozoal, and viral infections.

The term "tizoxanide", as used herein, relates to desacetyl-nitazoxanide, and is also referred to as 2-hydroxy-N-(5-nitro-2-thiazolyl)benzamide.

The term "idebenone", as used herein, relates to a drug initially developed for the treatment of Alzheimer's disease and other cognitive defects. Idebenone is also referred to as 2-(10-hydroxydecyl)-5,6-dimethoxy-3-methyl-1,4-benzoquinone.

The term "benzbromarone", as used herein, relates to a uricosuric agent and is also referred to as (3,5-dibromo-4-hydroxyphenyl) (2-ethyl-1-benzofuran-3-yl) methanone.

The term "dysregulated", as used herein, relates to the condition, in which mucus secretion and/or mucus production are abnormal, which may manifest in a pathological condition such as CF, ulcerative colitis, and irritable bowel syndrome. In one embodiment, dysregulated mucus secretion and/or mucus production relates to abnormally high levels of mucus in the respiratory tract and/or the gastrointestinal tract of the patient. In one embodiment, such pathological condition of abnormally high mucus secretion and/or mucus production is referred to as "disease characterized by dysregulated mucus secretion and/or mucus production". In many of the embodiments, "abnormal" refers to "pathologically increased" and/or "excess". In one embodiment, dysregulated may also relate to dysregulated bronchoconstriction, wherein bronchoconstriction is pathologically increased in a patient. In one embodiment, dysregulated may also relate to abnormal expression of inflammatory cytokines such as interleukin-8 and interleukin-13.

The term "substituted", as used herein, relates to an optional substitution of a residue with a chemical group, such as hydrogen, halogen, hydroxyl, amino, nitro, cyano, thiol, sulfonyl, carbonyl, carboxyl, alkyl, alkoxy, acetoxy, alkenyl, cycloalkyl, aryl, or heteroaryl. In one embodiment, a substituted group can have a substituent itself, such as aryl or heteroaryl having a substitution at one of its residues.

The term "cholinergic mucus secretion", as used herein, refers to mucus secretion which is triggered by cholinergic signaling. In one embodiment, "cholinergic mucus secretion" relates to muscarinic mucus secretion which is triggered by muscarinic signaling. In one embodiment, cholinergic mucus secretion is induced using methacholine (MCh) and/or carbachol (CCH). In one embodiment, cholinergic mucus secretion refers to muscarinic mucus secretion. In one embodiment, mucus release induced by cholinergic stimulation is independent of extracellular $Ca^{2+}$. Cholinergic secretion is due to binding of acetylcholine to basolateral receptors causing "compound exocytosis" which does not require TMEM16A. It may, however, require other TMEM16 proteins such as TMEM16F. In one embodiment, inhibiting TMEM16F results in indirect inhibition of cholinergic secretion by inhibition of mucus production.

The term "ATP-induced mucus secretion", as used herein, relates to a mechanism of mucus exocytosis which depends on ATP. In one embodiment, stimulation with ATP induces mucus secretion, and/or secretion of other molecules such as cytokines, in a cell. In one embodiment, ATP-induced mucus secretion is inhibited by inhibiting a TMEM16 protein, preferably TMEM16A and/or TMEM16F. In one embodiment, ATP-dependent secretion is characterized by $Ca^{2+}$ dependent single granule docking to the apical membrane requiring Munc13 proteins and the SNARE (soluble N-ethylmaleimide-sensitive factor attachment protein receptor) machinery. In one embodiment, ATP-induced mucus release occurs in native intestinal goblet cells upon stimulation with ATP, which have similar regulatory properties as mucus producing airway cells. In one embodiment, acute ATP-induced mucus secretion by airway club cells and colonic goblet cells is strongly compromised in the absence of TMEM16A, in contrast to cholinergic mucus secretion which is independent of TMEM16A. In one embodiment, ATP-induced mucus secretion is used synonymously with purinergic mucus secretion. In one embodiment, mucus secretion is used synonymously with mucus release.

The term "mucus", as used herein, refers to a liquid which is usually clear and thin, and protects the surface of organs such as the lungs. Distinct forms of mucin are produced in different organs, such as MUC2 being prevalently expressed in the intestine, and MUC5AC and MUC5B being the main forms found in the human airway. The term may also relate to pathophysiological mucus which is abnormally thick, sticky, and/or viscous. In one embodiment, mucus secretion and/or mucus production are inhibited by an inhibitor of TMEM16, preferably an inhibitor of TMEM16A and/or TMEM16F. In one embodiment, mucus secretion is inhibited by a TMEM16A inhibitor. In one embodiment, mucus secretion and/or mucus production are inhibited by a TMEM16F inhibitor.

The term "basal mucus secretion", as used herein, refers to mucus secretion independent of cholinergic induction. Basal mucus secretion is due to constituitive ATP release and binding to apical (luminal) purinergic receptors which increases intracellular $Ca^{2+}$ causing mucus release. In one embodiment, ATP-induced mucus secretion and basal mucus secretion are used synonymously. In one embodiment, basal mucus secretion is inhibited by an inhibitor of an TMEM16 protein, preferably by an inhibitor of TMEM16A and/or TMEM16F.

The term "release of pro-inflammatory cytokines", as used herein, refers to the release of pro-inflammatory cytokines, such as by secretion from immune cells, for example T helper cells and/or macrophages. In one embodiment, release of pro-inflammatory cytokines relates to release of interleukin-8 (IL-8). In one embodiment, LPS-induced release of IL-8 by Calu3 airway epithelial cells is significantly reduced by knockdown of TMEM16A (FIG. 12). In one embodiment, release of inflammatory cytokines by airway epithelial cells lacking TMEM16A is attenuated and may cause the reduced leukocytic infiltration observed in OVA-challenged animals (FIG. 4C). In one embodiment, inhibition of a TMEM16 protein, preferably of a TMEM16A and/or TMEM16F protein, results in the inhibition of secretion and/or production of a pro-inflammatory cytokine.

The term "pro-inflammatory cytokines", as used herein, refers to cytokines that are excreted from immune cells and that have a pro-inflammatory effect, i.e. such cytokines promote an immune response. Pro-inflammatory cytokines include interleukin-1, interleukin-8, interleukin-12, interleukin-18, tumor necrosis factor, and interferon gamma.

The term "goblet cell", as used herein, relates to a columnar epithelial cell that secretes gel-forming mucins, such as mucin MUC5A. A goblet cell is highly polarized, wherein the nucleus and other organelles are located at the base of the cell and secretory granules containing mucin are located at the apical surface. The apical plasma membrane has microvilli which allow for an increased surface area for secretion. Goblet cells are typically found in the respiratory, gastrointestinal, and reproductive tracts. In one embodiment, the term "goblet cell" relates to an "airway epithelial goblet cell". Differentiation of epithelial cells into goblet cells may result in excessive mucus production, such as in cystic fibrosis.

The term "club cells" or "Clara cells", as used herein, relates to dome-shaped cells with short microvilli which are found in the small airways, namely the bronchioles, of the lungs. Club cells may secrete molecules such as glycosaminoglycans to protect the bronchioles lining. In one embodiment, club cells relate to goblet cells which are not terminally differentiated. Typically, goblet cells have higher quantities of mucus than club cells.

The term "ciliated epithelial cells", as used herein, refers to epithelial cells having cilia. Ciliated epithelium is capable of moving particles or fluid over the epithelial surface in such structures as the trachea, bronchial tubes, and nasal cavities. Ciliated epithelial cells are often in the vicinity of mucus-secreting goblet cells.

The term "inhibiting", as used herein, refers to inhibiting signaling, such as of TMEM16A or of TMEM16F. In one embodiment, a compound for use according to the present invention is an inhibitor of a TMEM16 protein, such as TMEM16A or TMEM16F. In one embodiment, inhibiting TMEM16 signaling using an inhibitor results in inhibition of mucus secretion, inhibition of mucus production, inhibition of release of anti-inflammatory cytokines, and/or in bronchorelaxation. In one embodiment, blockade of a TMEM16 protein inhibits the release of mucus and cytokines, and induces bronchodilation, and thus has a beneficial effect in the treatment of inflammatory diseases and/or diseases characterized by dysregulated mucus secretion and/or mucus production. In one embodiment, blockade of a TMEM16 protein inhibits ATP-induced, i.e. basal mucus secretion. In one embodiment, blockade of a TMEM16 protein inhibits cholinergic mucus secretion indirectly by inhibiting mucus production. In many of the embodiments, when referring to a TMEM16 protein, it is particularly referred to a TMEM16A protein and/or a TMEM16F protein. In one embodiment, inhibiting TMEM16A and/or TMEM16F results in decreased mucus secretion, decreased mucus production, and/or decreased levels of inflammatory cytokines, and said decrease of mucus secretion, decrease of mucus production, and/or decrease of levels of inflammatory cytokines have beneficial effects in the treatment of a disease characterized by dysregulated mucus secretion and/or mucus production, preferably a disease selected from cystic fibrosis, ulcerative colitis, and/or irritable bowel syndrome.

The term "inhibitor", as used herein, relates to a compound that inhibits a target, such as a TMEM16 protein. In one embodiment, said inhibitor is an inhibitor of TMEM16A and/or TMEM16F. In one embodiment, said inhibitor is a specific inhibitor which exclusively binds to and inhibits one target, such as TMEM16A or TMEM16F. In one embodiment, said inhibitor may also have an effect on more than one target, i.e. an inhibitor may have an effect on different TMEM16 proteins, such as an effect on both TMEM16A and TMEM16F. In one embodiment, said inhibitor is selected from the group consisting of niclosamide, niclosamide ethanolamine salt, nitazoxanide, tizoxanide, benzbromarone, idebenone, and any compound having a structure according to any of Formula I, Formula II, Formula III, and Formula IV.

The term "TMEM16", as used herein, relates to proteins which are also known as anoctamins, and which are involved in the variety of functions including ion transport and regulation of other membrane proteins. TMEM16 proteins are a family of proteins comprising TMEM16A, TMEM16B, TMEM16C, TMEM16D, TMEM16E, TMEM16F, TMEM16G, TMEM16H, TMEM16J, and TMEM16K. TMEM16A and TMEM16B function as $Ca^{2+}$-activated $Cl^-$ channels. TMEM16 proteins are expressed ubiquitously, for example in mucus-producing cells, in smooth muscle cells of the airways, and in immune cells. In one embodiment, TMEM16A is essential for basal secretion of mucus in airways and intestine, as airway and intestinal epithelial specific knockout of TMEM16A leads to accumulation of mucus in airway club (Clara) cells, airway goblet cells, and intestinal goblet cells. In one embodiment, TMEM16F is essential for basal secretion of mucus in airways and intestine, as airway and intestinal epithelial specific knockout of TMEM16A leads to accumulation of mucus in airway club (Clara) cells and intestinal goblet cells. In one embodiment, TMEM16 is preferably TMEM16A and/or TMEM16F. In one embodiment, TMEM16 is any of TMEM16A, TMEM16B, TMEM16C, TMEM16D, TMEM16E, TMEM16F, TMEM16G, TMEM16H, TMEM16J, and TMEM16K.

The term "a disease affecting the respiratory tract and/or the gastrointestinal tract", as used herein, relates to a disease of the respiratory tract and/or the gastrointestinal tract, wherein said disease may have symptoms concerning the respiratory tract or the gastrointestinal tract or both. In one embodiment, said disease affecting the respiratory tract and/or the gastrointestinal tract is selected from cystic fibrosis, ulcerative colitis, and irritable bowel syndrome.

The term "cystic fibrosis" or "CF", as used herein, relates to a disorder that affects mostly the lungs, but also other organs, such as the intestine. Cystic fibrosis (CF) may cause difficult breathing and coughing, due to abnormal mucus homeostasis including abnormal thickening of mucus. CF is mostly accompanied by viscous mucus in the airways and may also be accompanied by viscous mucus in the intestine and/or bronchoconstriction. CF is associated with the presence of mutations in the gene for the cystic fibrosis transmembrane conductance regulator (CFTR). CFTR protein is a chloride ion channel and is involved in creating sweat, digestive juices, and airway surface liquid. In one embodiment, CF relates to a CF condition which comprises one or more of the following conditions; goblet cell metaplasia, abnormal mucus production, airway constriction, lung atelectasis, and/or bronchoconstriction. In one embodiment, a patient having CF is affected by distal intestinal obstruction syndrome (DIOS) which arises from abnormal intestinal mucus production. In one embodiment, a patient to be treated with a compound for use according to the present invention is characterized by having a specific subset of the above CF manifestations.

The term "ulcerative colitis", as herein, refers to a condition which is associated with inflammation and ulcers of the colon and rectum. Ulcerative colitis is an inflammatory bowel disease. In one embodiment, ulcerative colitis is characterized by dysregulated mucus secretion and/or production.

The term "irritable bowel syndrome", as used herein, relates to a group of symptoms which includes abdominal pain and changes in the pattern of bowel movements. Irritable bowel syndrome is a chronic gastrointestinal bowel disorder causing diarrhea, abdominal pain, cramps, bloating and gas. In one embodiment, irritable bowel syndrome is characterized by dysregulated mucus secretion and/or production.

The term "administered", as used herein, refers to application of a compound to a patient having a disease characterized by dysregulated mucus secretion and/or mucus production. Said application can be performed topically or systemically, such as an oral, nasal, mucosal, intrabronchial, intrapulmonar, intradermal, subcutaneous, intravenous, intramuscular, intravascular, intrathecal, intraocular, intraarticular, or intranodal administration. In a preferred embodiment, said compound is administered orally, nasally, mucosally, intrabronchially, or intrapulmonarily. Said administration of a compound can be performed using various routes, such as tablets, pills, sprays, aerosols, inhalators, suppositories, or infusions.

The term "Penh" or "enhanced pause", as used herein, relates to a measurement of the airflow pattern entering and leaving a whole-body flow plethysmograph as an animal breathes.

BRIEF DESCRIPTION OF THE FIGURES

The present invention is now further described by reference to the following figures.

A) Airways in control conditions without allergization.
B) Airways after allergization with ovalbumin resulting in development of an asthma-like immune response. Excessive mucus production is observed by Alcian blue staining. Furthermore, inflammatory infiltration with immune cells is observed.
C) Activation of cholinergic receptors with the muscarinic agonist carbachol (CCH). The airways are constricted. The mucus is partially secreted.
D) 3-day treatment using niclosamide reduces the CCH-induced constriction of the airways. Mucus secretion and inflammatory infiltrates are reduced.

Figure 2:
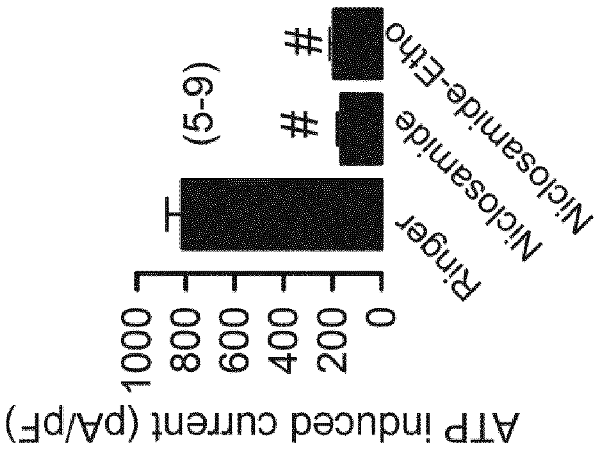

FIG. 2: ATP-induced current in HT29 cells expressing TMEM16A in an electrophysiological patch clamp investigation.

ATP was applied at a concentration of 100 μM. Simultaneous application of 1 μM niclosamide or 1 μM niclosamide-ethanolamin inhibits the activation of TMEM16A significantly ($^{\#}$p<0.01). The ATP-induced ion current arising from TMEM16A activation is significantly reduced by niclosamide or niclosamide-ethanolamin in patch clamp analysis.

Figure 3:
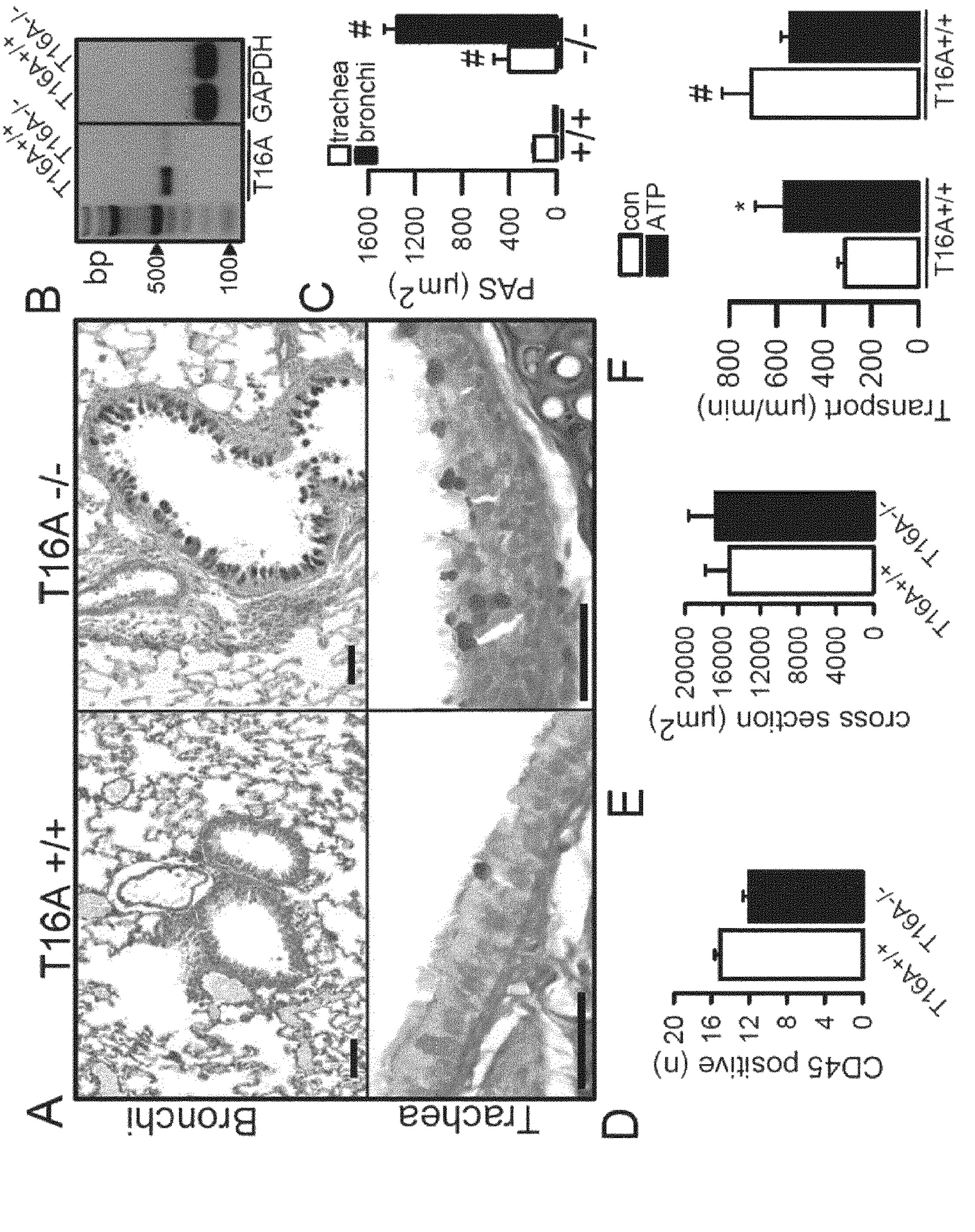

FIG. 3: Accumulation of mucus in airways of TMEM16A−/− mice.

A) Mucus staining by periodic acid-Schiff staining (PAS) in bronchi and tracheas of TMEM16A+/+ and TMEM16A−/− mice, indicating accumulation of mucus in airways of T16A−/− mice. Bars indicate 20 μm.

B) RT-PCR analysis of TMEM16A in isolated respiratory epithelial cells from T16A+/+ and T16A−/− mice.

C) PAS positive staining in T16A+/+ and T16A−/− airways (n=29).

D) Number of CD45 positive cells (airways) under different conditions (n=20).

E) Cross sectional area of airways from T16A+/+ and T16A−/− mice (n=20).

F) Mucociliary transport and effect of carbachol (CCH) or ATP (both 100 μM) assessed by particle tracking in tracheas from T16A+/+ and T16F−/− animals (n=17). Mean±SEM; *significant difference when compared to T16A+/+ (paired t-test); $^{\#}$significant difference when compared to T16A+/+ (unpaired t-test).

Figure 4:
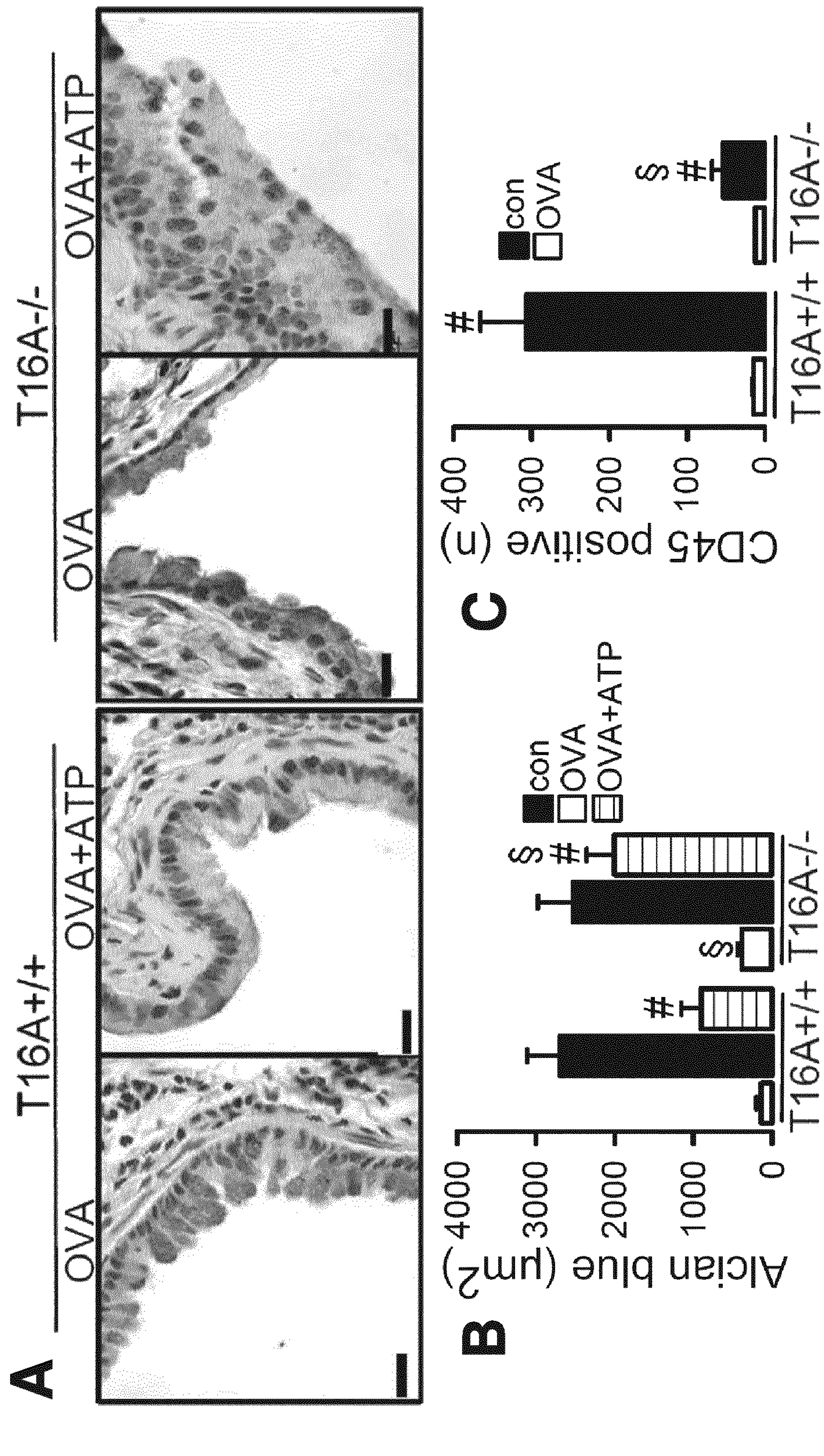

FIG. 4: Defective mucus secretion in airways of TMEM16A−/− mice.

A) Expression of mucus induced by OVA-sensitization in airways of T16A+/+ and T16A−/− animals, as detected by alcian blue staining. Exposure to ATP (100 μM) induces release of mucus in T16A+/+ airways, which is attenuated in T16A−/− mice. Bars indicate 10 μm.

B) Quantification of alcian blue stainings (n=10-16).

C) Number of CD45 positive cells in lungs from control and OVA-sensitized animals (n=10-16). Mean±SEM; #significant effect of ATP or OVA, respectively (unpaired t-test); ssignificant difference when compared to T16A+/+ (unpaired t-test).

Figure 5:
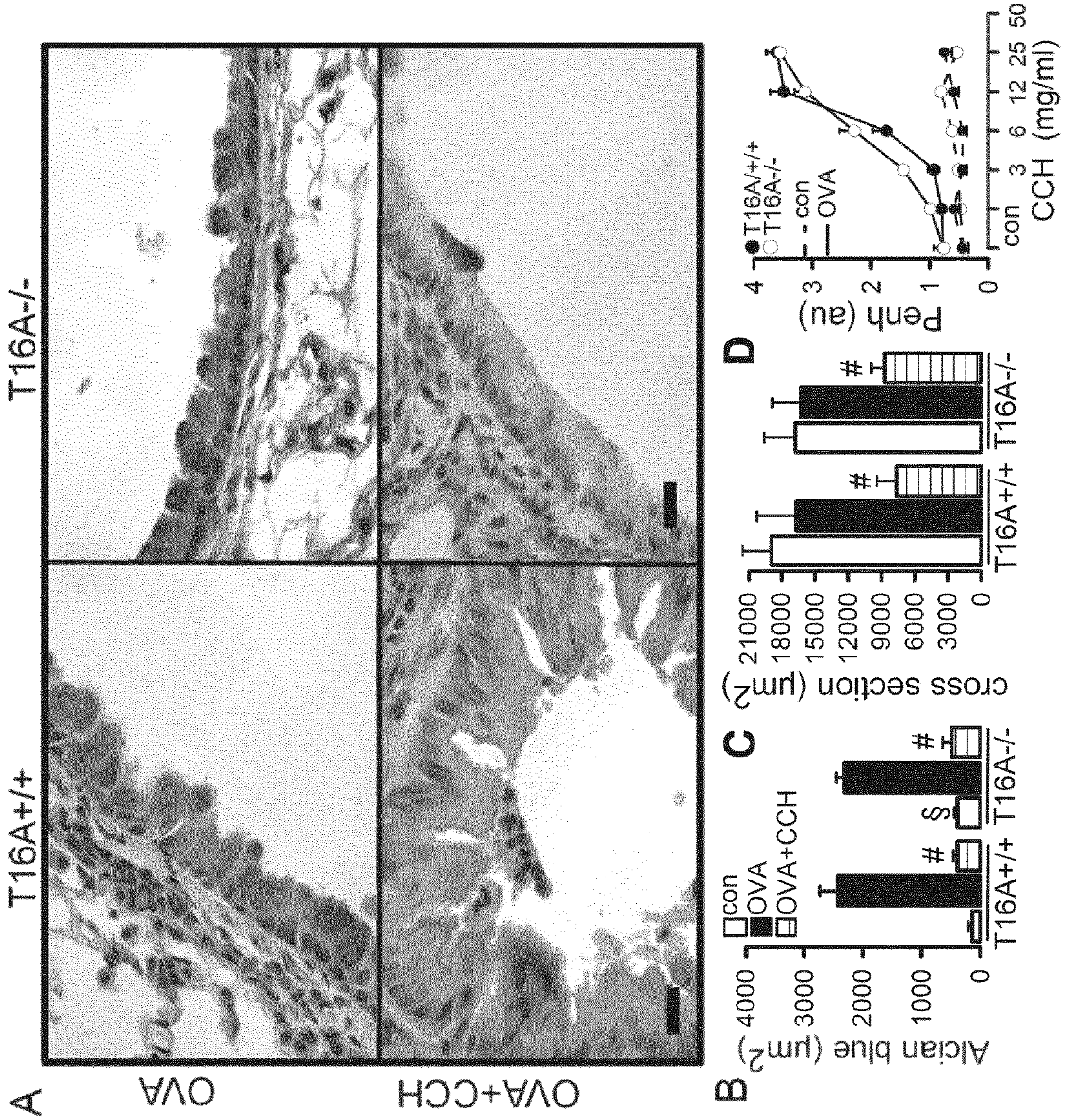

FIG. 5: Compromised mucus secretion in airways of OVA-sensitized TMEM16A−/− mice.

A) Mucus production induced by OVA-sensitization in airways from TMEM16A+/+ (T16A+/+) and TMEM16A−/− (T16A−/−) mice, and carbachol (CCH; 100 μM) induced mucus release. Bars indicate 10 μm.

B) Summary of alcian blue staining indicating strong increase of mucus production by OVA-sensitization and release of mucus by stimulation with CCH (n=23).

C) Effect of OVA-sensitization and CCH on cross sectional area of airways from T16A+/+ and T16A−/− mice (n=23).

D) Enhanced pause (Penh) assessed under CCH-exposure in T16A+/+ and T16A−/− mice (n=5) indicating that CCH-induced airway constriction is not affected by epithelial knockout of TMEM16A. Mean±SEM; #significant difference when compared to OVA (unpaired t-test); ssignificant difference when compared to T16A+/+ (unpaired t-test).

Figure 6:
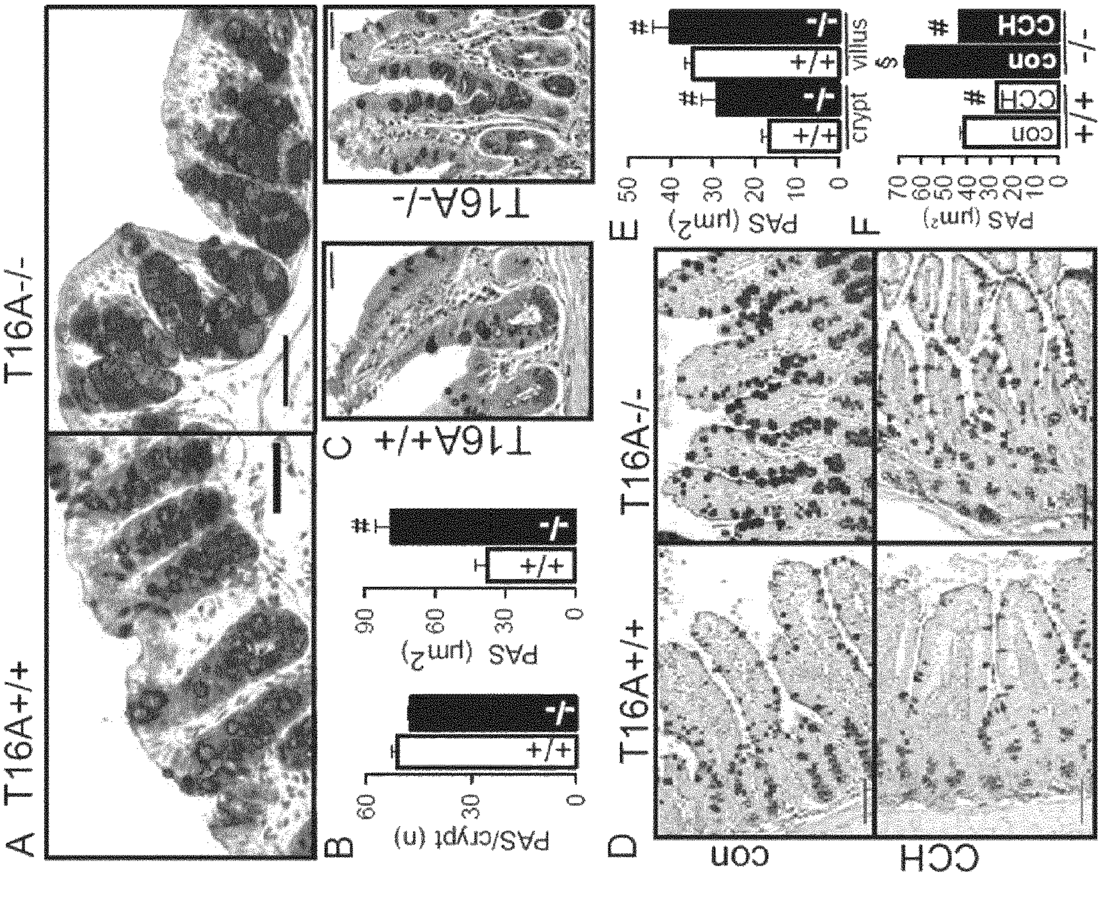

FIG. 6: Enhanced mucus in intestinal goblet cells of TMEM16A−/− mice.

A) PAS-staining of large intestinal goblet cells from TMEM16A+/+ (T16A+/+) and TMEM16A−/− (T16A−/−) mice.

B) Number of PAS-positive cells and PAS-positive area in crypts from T16A+/+ and T16A−/− mice (n=40).

C,D) PAS staining in small intestine of T16A+/+ and T16A−/− mice (C) and effect of CCH (100 UM) (D).

E) PAS staining in crypts and villi of T16A+/+ and T16A−/− mice (n=550-750).

F) Effect of CCH on PAS staining in T16A+/+ and T16A−/− mice (n=550-750). Mean±SEM; #significant difference when compared to T16A+/+ or control, respectively (unpaired t-test).

Figure 7:
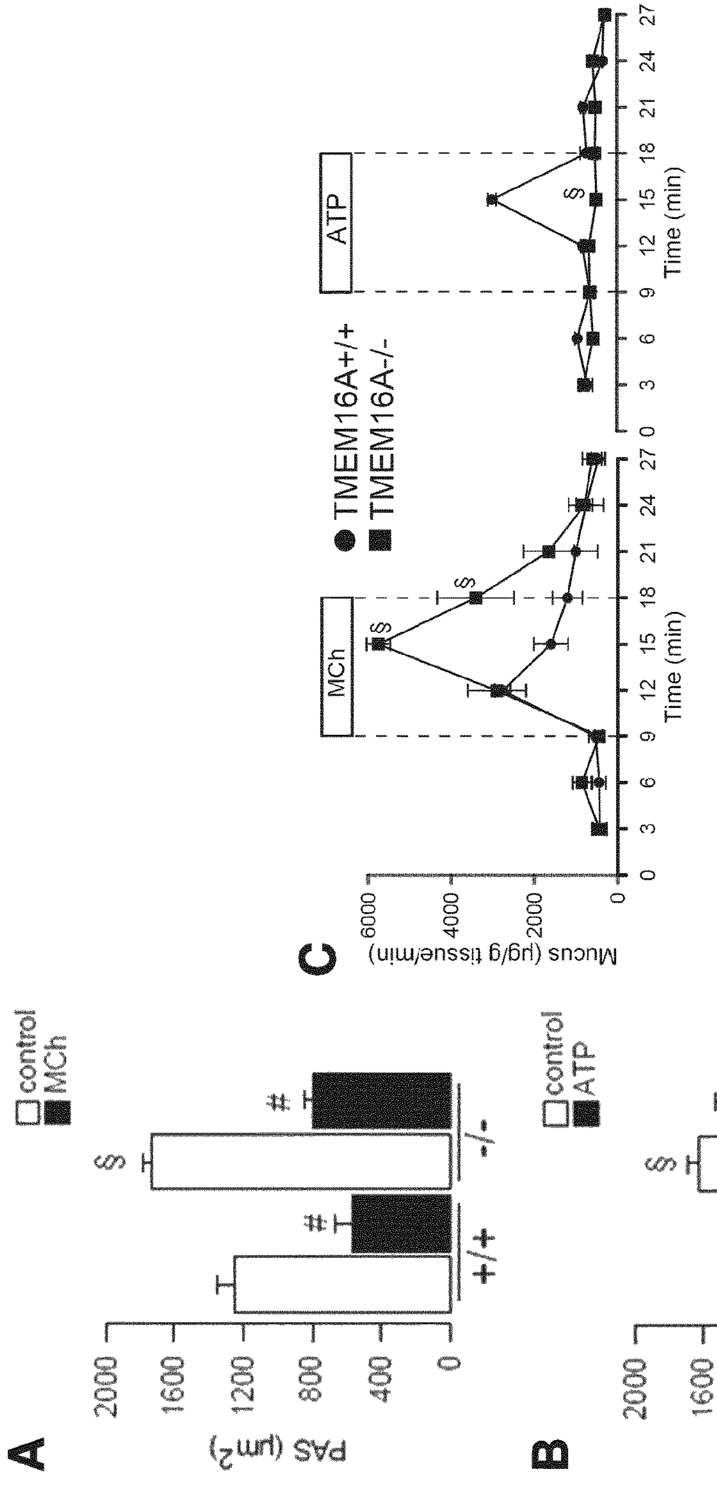

FIG. 7: Compromised mucus release in TMEM16A−/− intestine.

A,B) Quantification of PAS before and after stimulation with MCh (A) or ATP (B) (n=19-34). Mean±SEM; #significant difference when compared to control (unpaired t-test). $^{\S}$ significant difference when compared to T16A+/+ (unpaired t-test).

C) Acute mucus secretion in perfused colon from TMEM16A+/+ (black) and TMEM16−/− (red) animals. Mucus release was induced by luminal/basolateral perfusion with methacholine or ATP, respectively.

Figure 8:
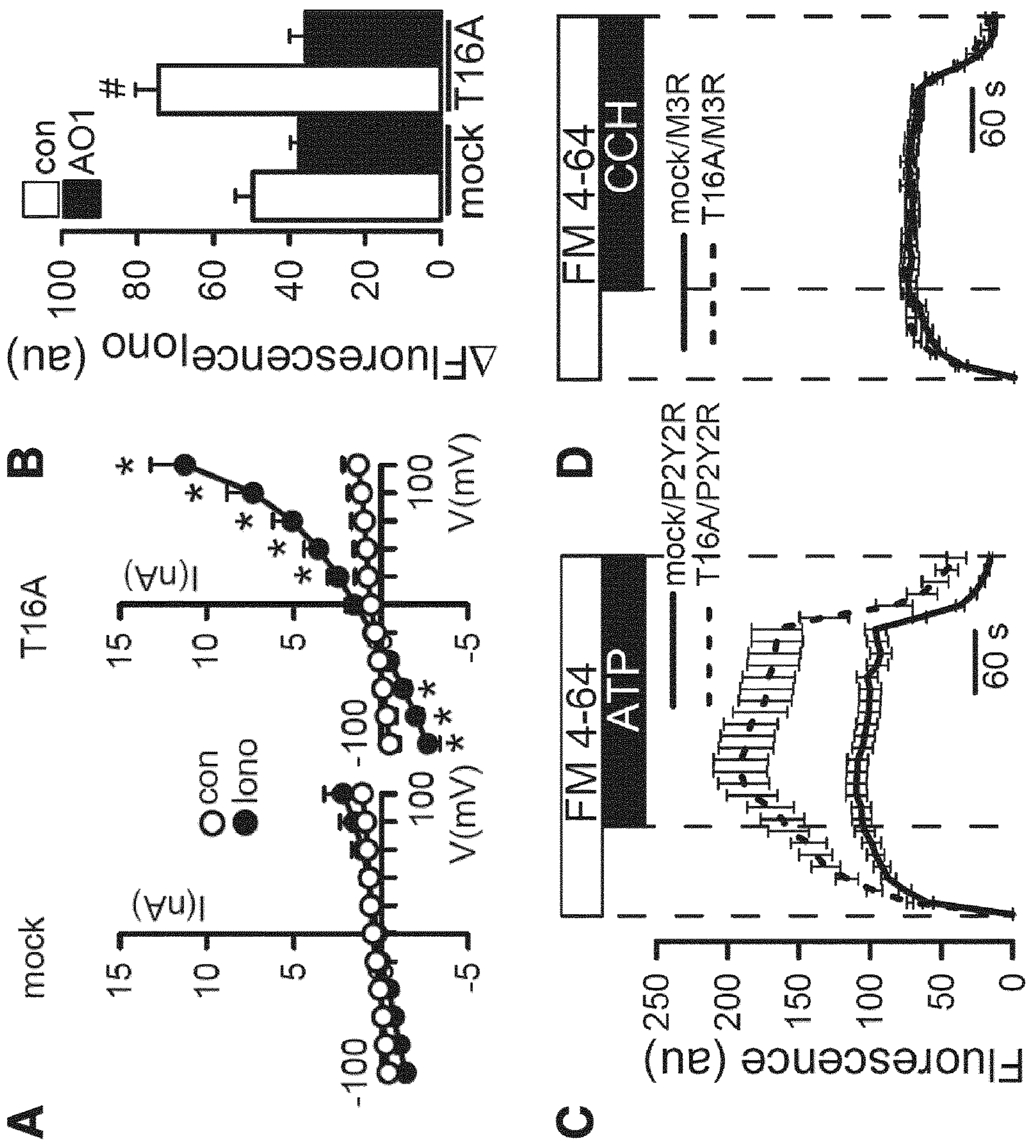

FIG. 8: TMEM16A controls exocytosis.

A) Whole cell current/voltage relationships obtained in mock transfected and TMEM16A (T16A) expressing HEK293 cells. Stimulation with the Ca2+ ionophore ionomycin (Iono; 1 M) activated whole cell currents in TMEM16A-expressing cells (n=12).

B) Increase of FM4-64 fluorescence upon stimulation with ionomycin in mock-transfected and TMEM16A-expressing cells, and inhibition by CaCCinhAO1 (AO1; 10 μM) (n=30).

C) Effect of ATP, or

D) CCH (both 100 μM) on FM4-64 fluorescence in cells expressing P2Y2 or M3 receptors (n=30). Mean±SEM. *significant increase by Iono (paired t-test). #significant difference when compared to mock (unpaired t-test).

Figure 9:
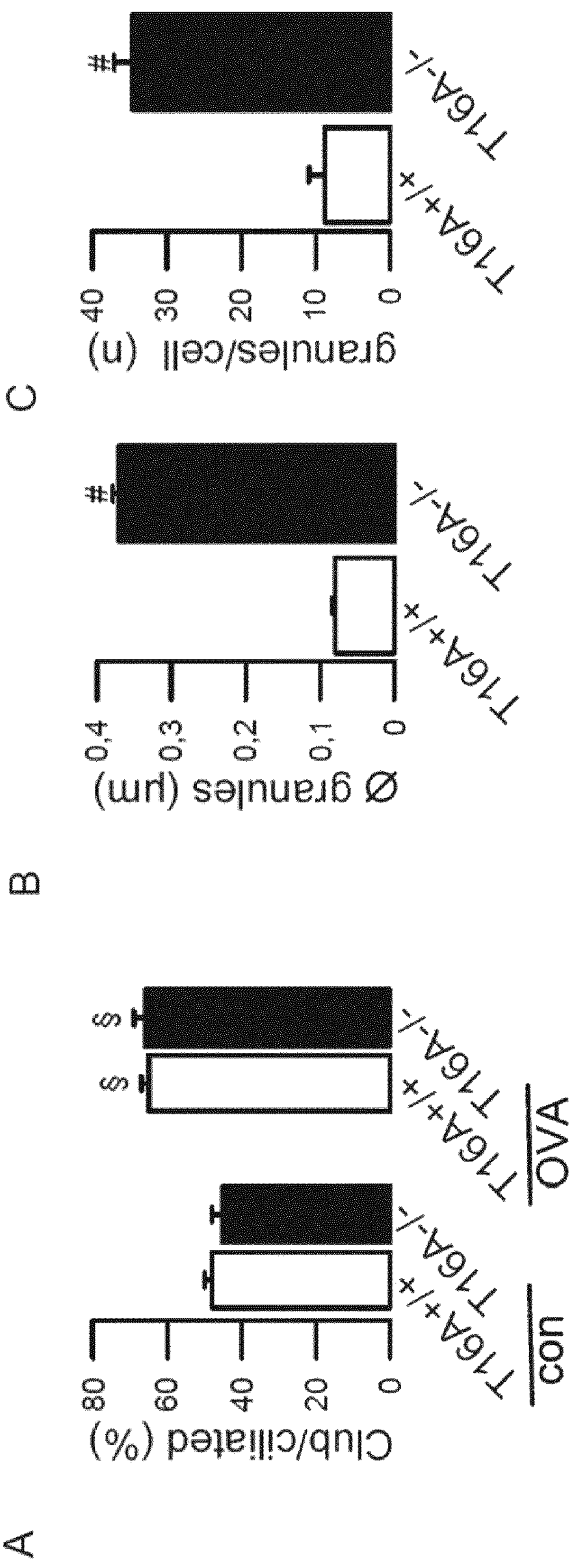

FIG. 9: Club cells and secretory granules from TMEM16A+/+ and TMEM16A−/− airways.

A) Ratio of club cells (Clara cell specific protein, CCSP positivity) versus ciliated (acetylated tubulin positive) cells in small airways. Loss of TMEM16A does not increase the number of club cells under control conditions. Ovalbumin-sensitization enhanced the number of club cells in both wild type and knockout mice. § indicates significant difference between control and OVA-treated animals (p<0.5; unpaired t-test).

B) Diameter of secretory granules in club cells of TMEM16A+/+ and TMEM16A−/− cells.

C) Number of granules per cell in club cells of TMEM16A+/+ and TMEM16A−/− cells. # indicates significant difference between TMEM16A+/+ and TMEM16A−/− (p<0.5; unpaired t-test).

Figure 10:
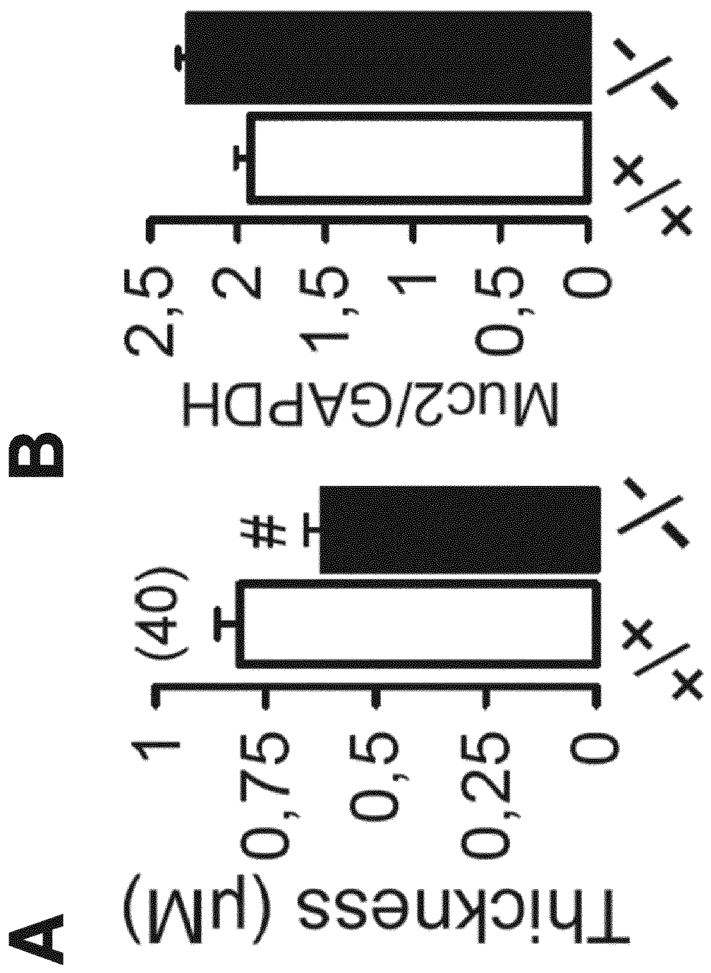

FIG. 10: Defective mucus secretion in small intestine in TMEM16A−/− mice.

A) PAS staining of mucus covering jejunal mucosa of TMEM16A+/+ and TMEM16A−/− mice. The mucus layer in TMEM16A−/− intestine appeared thinner and more irregular.

B) mRNA levels of Muc2 in TMEM16A+/+ and TMEM16A−/− colon as assessed by semiquantitative RT-PCR.

Figure 11:
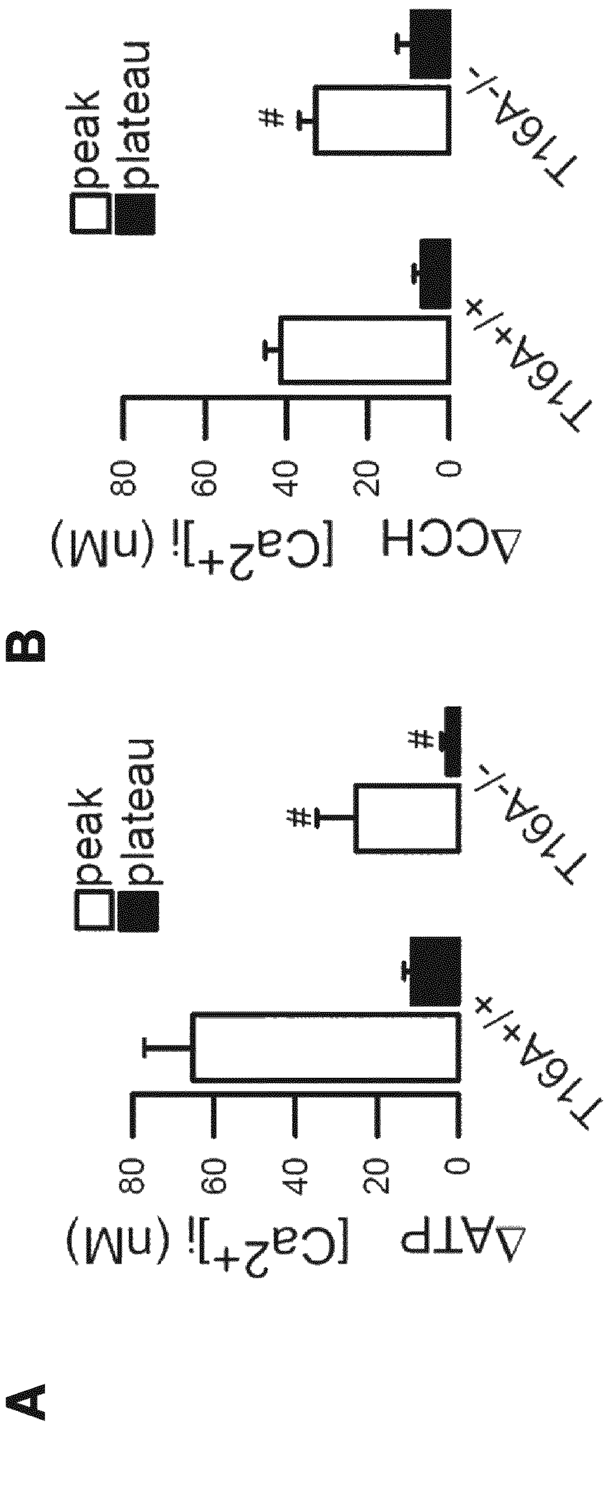

FIG. 11: Purinergic $Ca^{2+}$ signals are compromised in goblet cells from TMEM16A−/− colon.

A) ATP-induced $Ca^{2+}$ increase (peak and plateau) is strongly reduced in goblet cells from TMEM16A−/− mice.

B) $Ca^{2+}$ peaks induced by carbachol (CCH; 100 μM) were only slightly reduced in TMEM16A−/− cells. #indicates significant difference from TMEM16A+/+.

Figure 12:
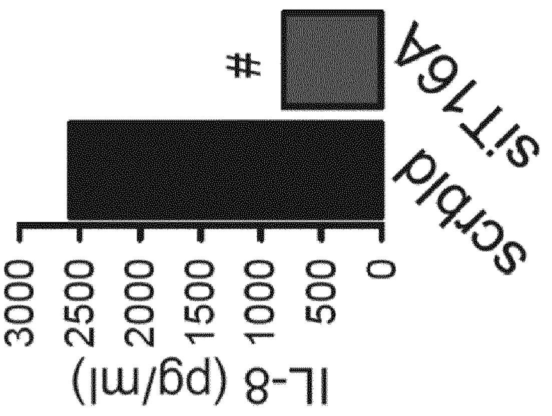

FIG. 12: IL-8 release from Calu3 human airway submucosal cells.

Exposure of the cells to LPS (10 μg/ml; 48 h) induced a pronounced IL-8 release (scrbld; scrambled RNA) that was markedly reduced upon inhibition of TMEM16A signaling using siRNA for TMEM16A.

Figure 13:
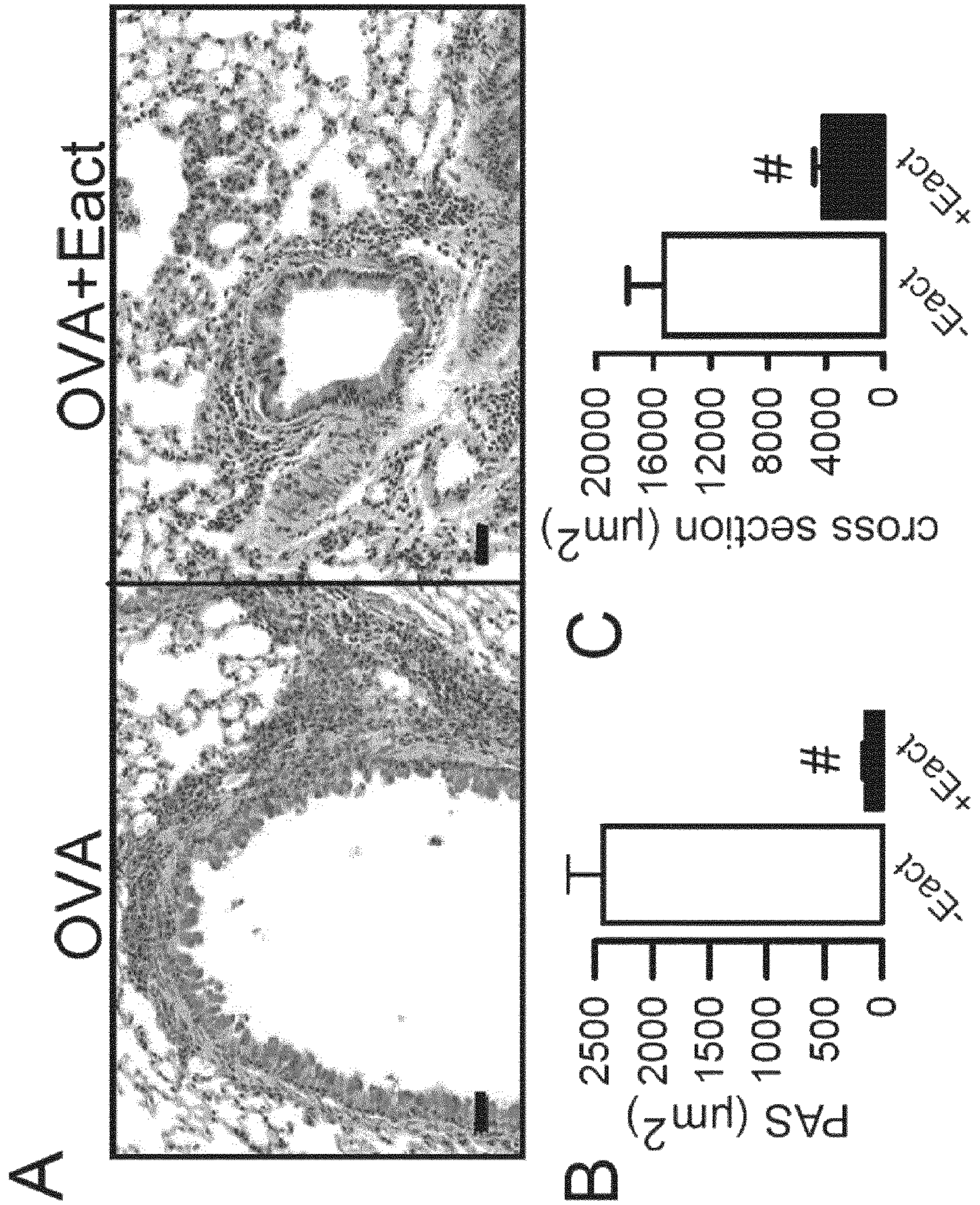

FIG. 13: Activation of TMEM16A by Eact inducing mucus release and bronchoconstriction.

Activation of TMEM16A in OVA-sensitized mice shows that activation of TMEM16A by Eact induces massive mucus release and airway contraction.

A) Airways from OVA-sensitized mice show pronounced mucus accumulation as demonstrated by alcian blue staining. Acute exposure to the known activator of TMEM16A, Eact, induces a rapid mucus release and airway contraction. Bars indicate 10 μm.

B) PAS positive staining in control airways (OVA) and after application of Eact.

C) Airway cross sectional area in control airways and after application of Eact. # indicates significant effect of Eact.

Figure 14:
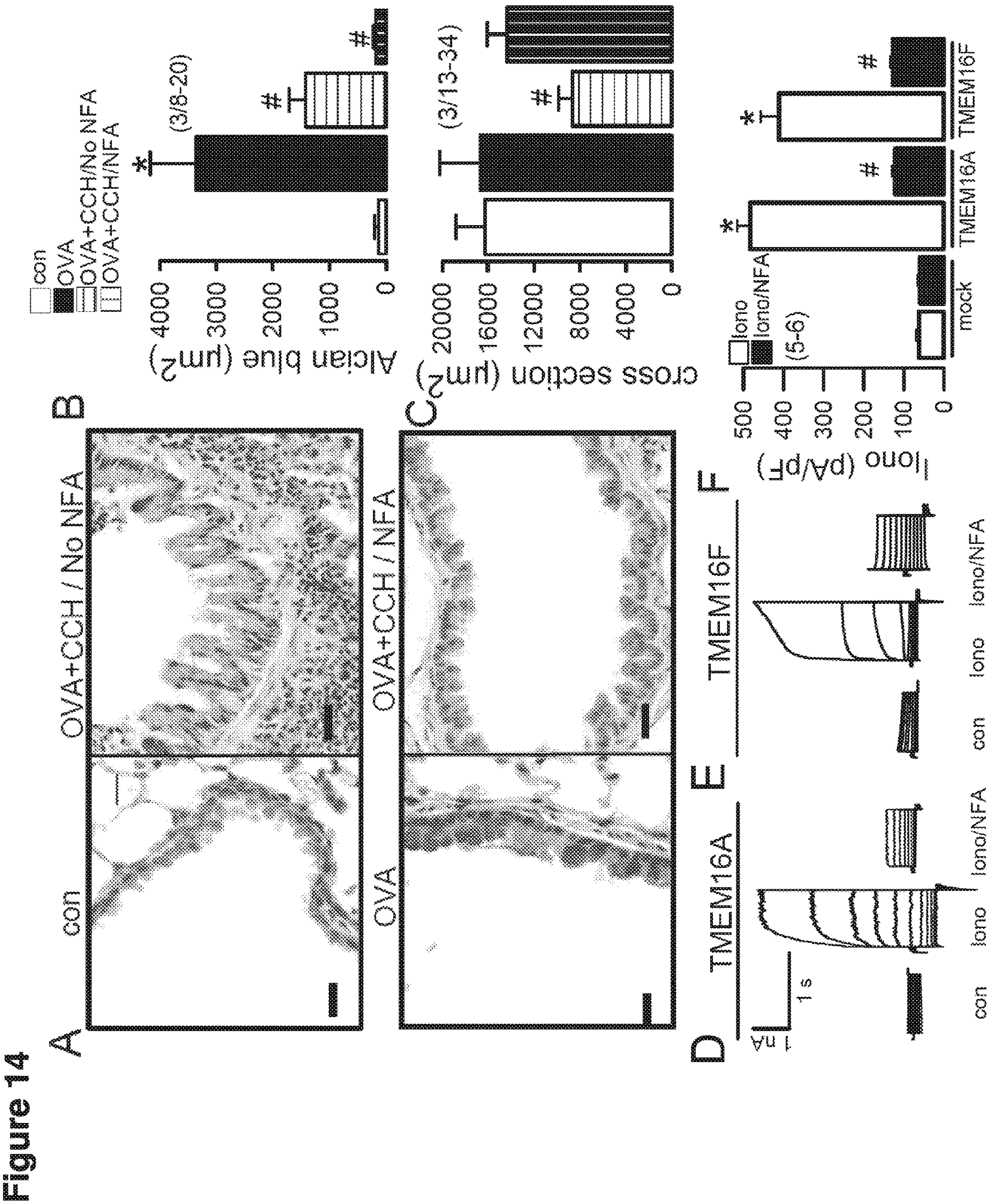

FIG. 14: The TMEM16-inhibitor niflumic acid attenuates inflammatory airway disease.

A,B) OVA-sensitization induced pronounced goblet cell metaplasia as indicated by alcian blue positivity. Exposure to carbachol (CCH, 25 mg/ml, nebulizer) induced release of mucus and airway relaxation. Bars indicate 10 μm. Pre-exposure to the TMEM16A-inhibitor niflumic acid (NFA, 20 mg/kg/day) by intratracheal application for three days, strongly attenuated mucus production and CCH-induced airway contraction (A-C).

C) Cross section of airways under the 18 different conditions indicating airway relaxation by NFA.

D-F) Whole cell currents obtained in HEK293 cells expressing TMEM16A or TMEM16F after stimulation with 1 μM ionomycin (Iono), and inhibition by NFA (20 μM). Mean±SEM; *significant inhibition by NFA (paired ttest). #significant difference when compared to OVA (unpaired t-test). (n) number of airways analysed or number of cells examined.

Figure 15:
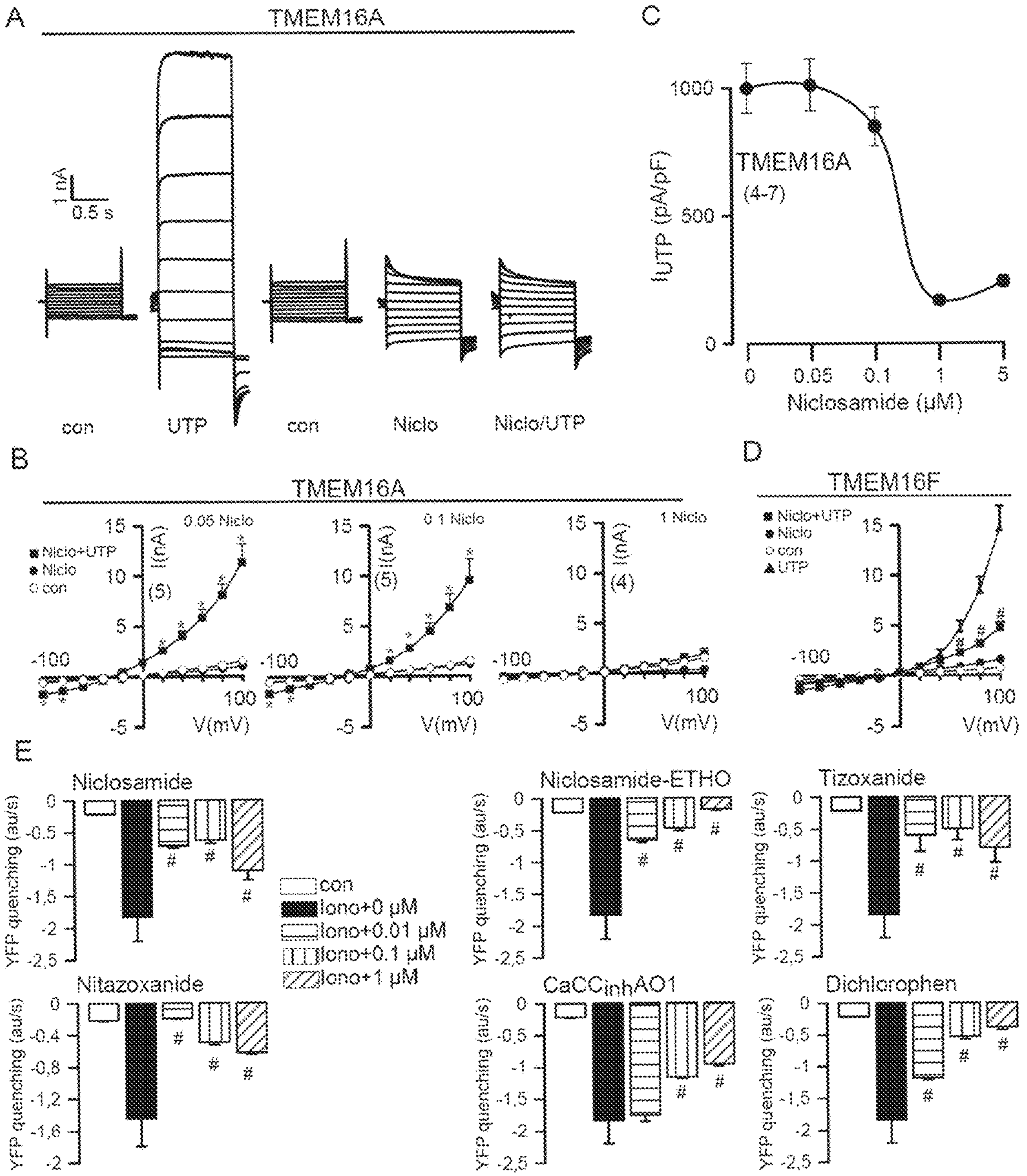

FIG. 15: Inhibition of TMEM16A and TMEM16F by niclosamide.

A) TMEM16A whole cell currents in overexpressing HEK293 cells. The purinergic agonist UTP was used to activate TMEM16A (100 UM).

B,C) Concentration-dependent inhibition of TMEM16A by niclosamide (Niclo).

D) Current/voltage relationship showing inhibition of TMEM16F by niclosamide (1 μM).

E) Inhibition of endogenous TMEM16A/F expressed in HT29 cells, as shown by iodide quenching. Rate of YFP quenching (arbitrary units (au/second), when applying 20 mM iodide to the extracellular bath solution. HT29 cells stably overexpressing YFP were stimulated with 1 M ionomycin. 100.000 cells were seeded/well. Mean±SEM; (number of experiments) #significant inhibition when compared to the absence of the inhibitor ($p<0.05$; unpaired t-test); *significant activation by UTP (paired t-test).

Figure 16:
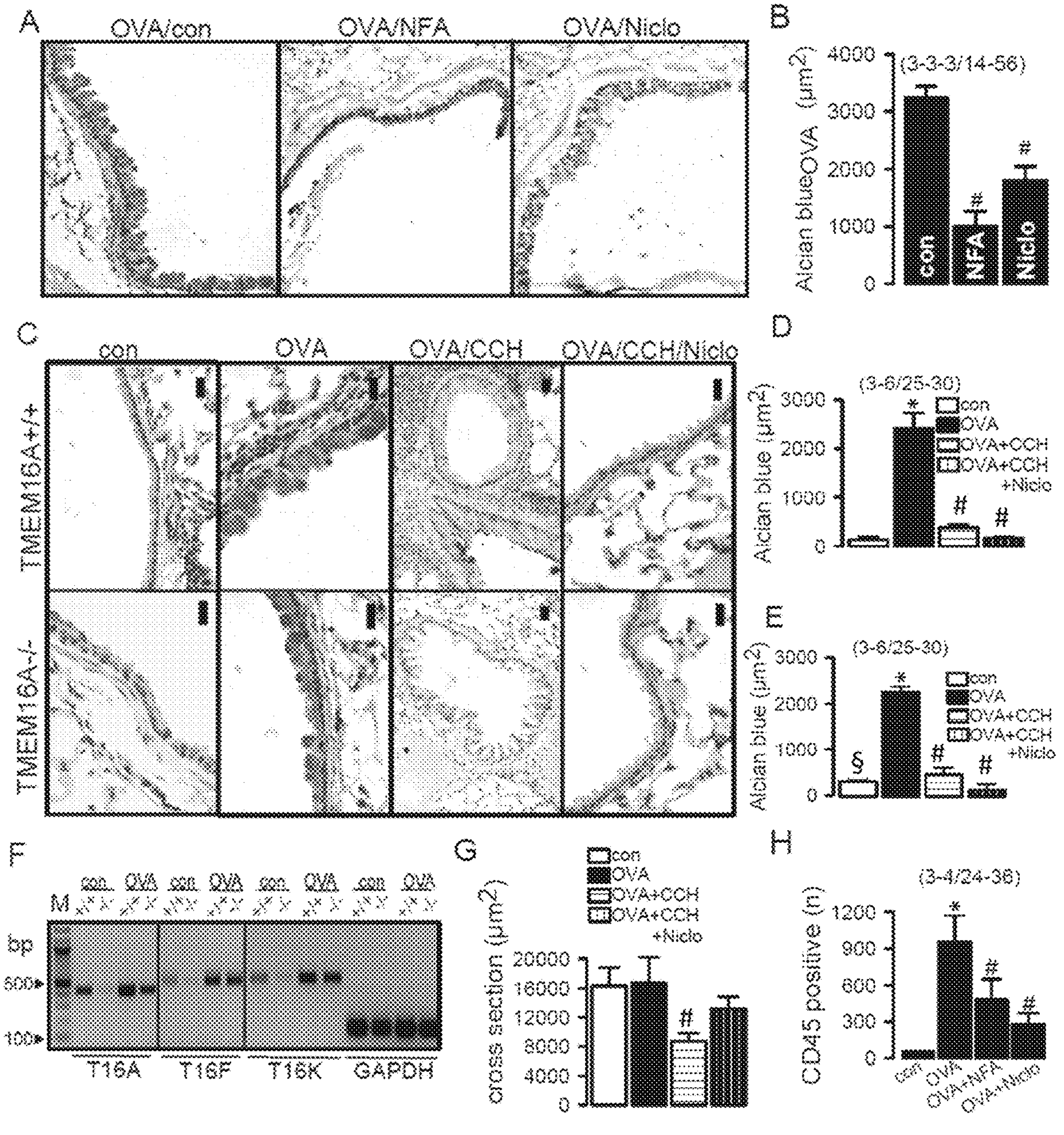

FIG. 16: Niclosamide attenuates inflammatory airway disease.

A,B) OVA-sensitization of wt mice induced pronounced goblet cell metaplasia as indicated by alcian blue staining. Application of niflumic acid (20 μM) or niclosamide (5 μM) per tracheal instillation inhibited mucus production.

C-E) OVA-sensitization of TMEM16A$^{flox/flox}$ (TMEM16A+/+) and FoxJ1-Cre-TMEM16A$^{flox/flox}$ (TMEM16A−/−) mice induced goblet cell metaplasia. Exposure of TMEM16A$^{flox/flox}$ (TMEM16A+/+) and FoxJ1-Cre-TMEM16A$^{flox/flox}$ (TMEM16A−/−) mice to carbachol (CCH, 25 mg/ml, nebulizer) induced release of mucus and pronounced airway contraction. Pre-exposure to niclosamide by intratracheal application for three days strongly attenuated mucus production and CCH-induced airway contraction.

F) Expression of the three main TMEM16 paralogs (A,F, K) in mouse airways before and after OVA-sensitization. Bars indicate 10 μm.

G) Airway cross section indicating airway contraction by muscarinic stimulation (aerosol) and inhibition of contraction by niclosamide.

H) Number of CD45 positive cells (airways) under different conditions. Mean±SEM; (number of experiments) #significant difference when compared to the absence of CCH ($p<0.05$; ANOVA); *significant increase by OVA (unpaired t-test); § significant difference when compared to control (unpaired t-test).

Figure 17:
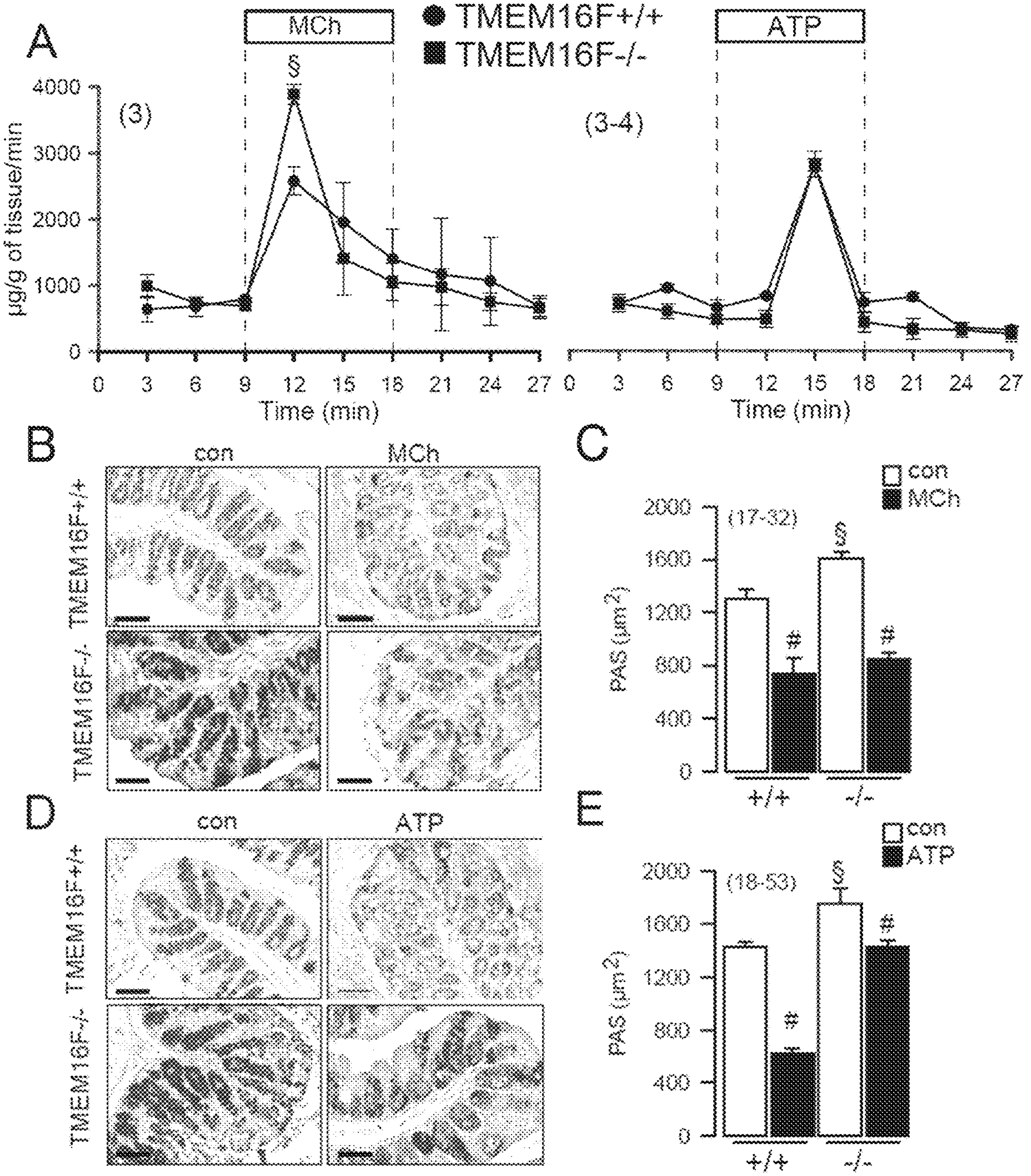

FIG. 17: Mucus release in TMEM16F−/− intestine.

A) Acute mucus secretion in excised colon from TMEM16F+/+ and TMEM16F−/− animals. Mucus release was assessed in in vitro perfused colon and was induced by luminal/basolateral perfusion with methacholine (100 μM) or ATP (100 μM), respectively. Inset shows lack of TMEM16F expression in colonic crypt cells of TMEM16F−/− animals by RT-PCR.

B-E) PAS staining of proximal colon before and after stimulation with methacholine (100 μM) (B,C) or ATP (100 μM) (D,E). Bars indicate 50 μm. Mean±SEM; #significant difference when compared to control (unpaired t-test). § significant difference when compared to TMEM16A+/+ (unpaired t-test). (n) number of perfused colons and PAS stainings, respectively.

Figure 18:
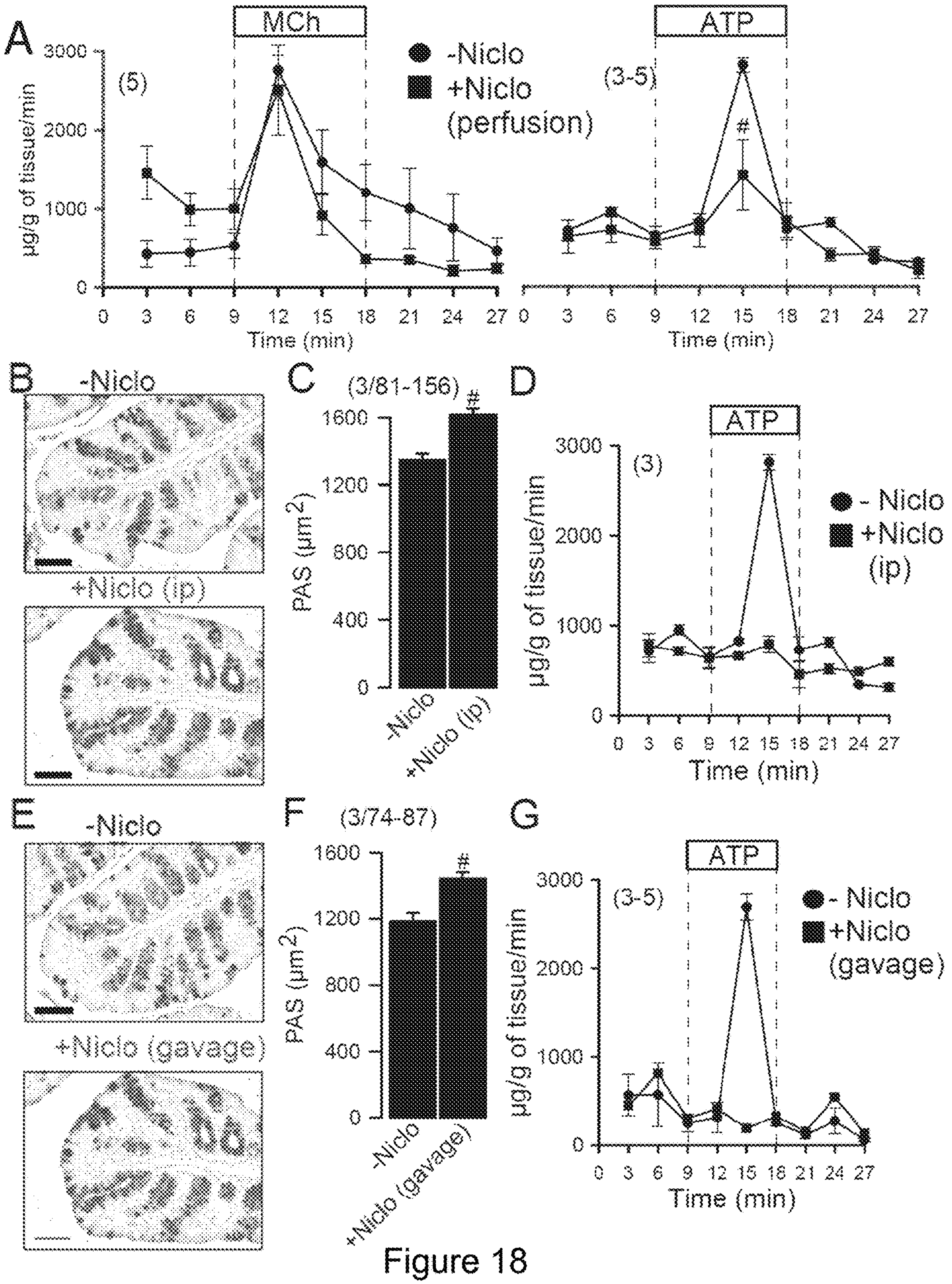

FIG. 18: Effect of niclosamide on intestinal mucus release.

A) Acute mucus secretion in excised wt colon activated by methacholine or ATP, respectively, and inhibition by acute perfusion with niclosamide (niclosamide; 10 μM).

B-D) Effect of intraperitoneal injection of niclosamide (20 mg/kg/day) on PAS staining (B,C) and acute mucus discharge induced by perfusion with 100 μM ATP (D).

E-G) Effect of application of niclosamide by gavage (20 mg/kg/day) on PAS staining (E,F) and acute mucus discharge induced by perfusion with 100 μM ATP (G). Mean±SEM; #significant difference when compared to -niclosamide (unpaired t-test); (n) number of perfused colons and PAS stainings analyzed, respectively. Bars indicate 50 μm.

Figure 19:
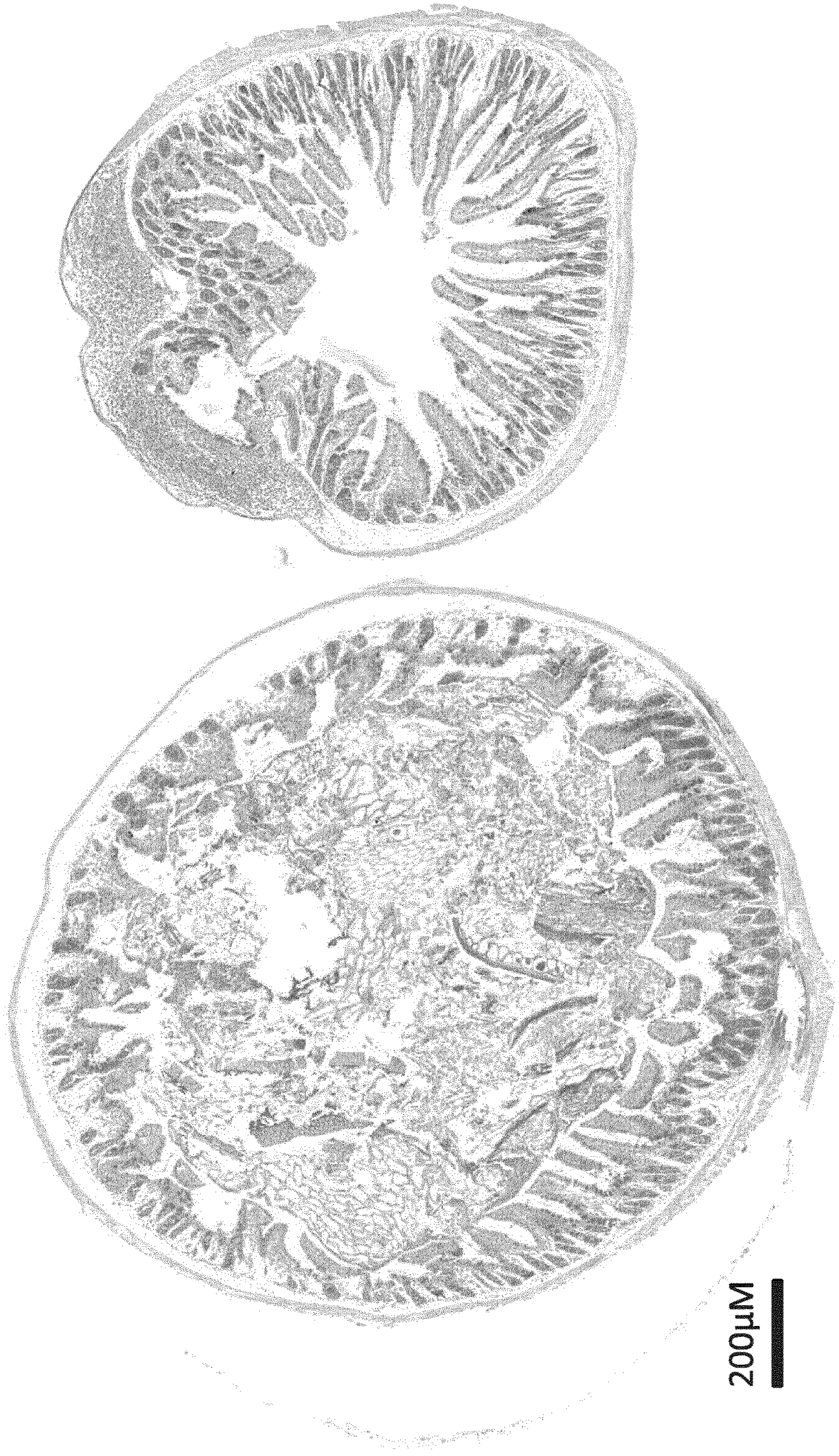

FIG. 19: Mucus staining by alcian blue in jejunum from mice homozygous for the cystic fibrosis mutation CFTR$^{deltaF508/deltaF508}$.

A) Sham treated mice (intraperitoneal injection of corn oil for 7 days) demonstrate significant amounts of mucus in the intestinal lumen.

B) Animals injected intraperitoneally for 7 days with niclosamide (13 mg/kg/day, dissolved in corn oil) demonstrate smaller jejunal diameters and largely reduced mucus.

Figure 20:
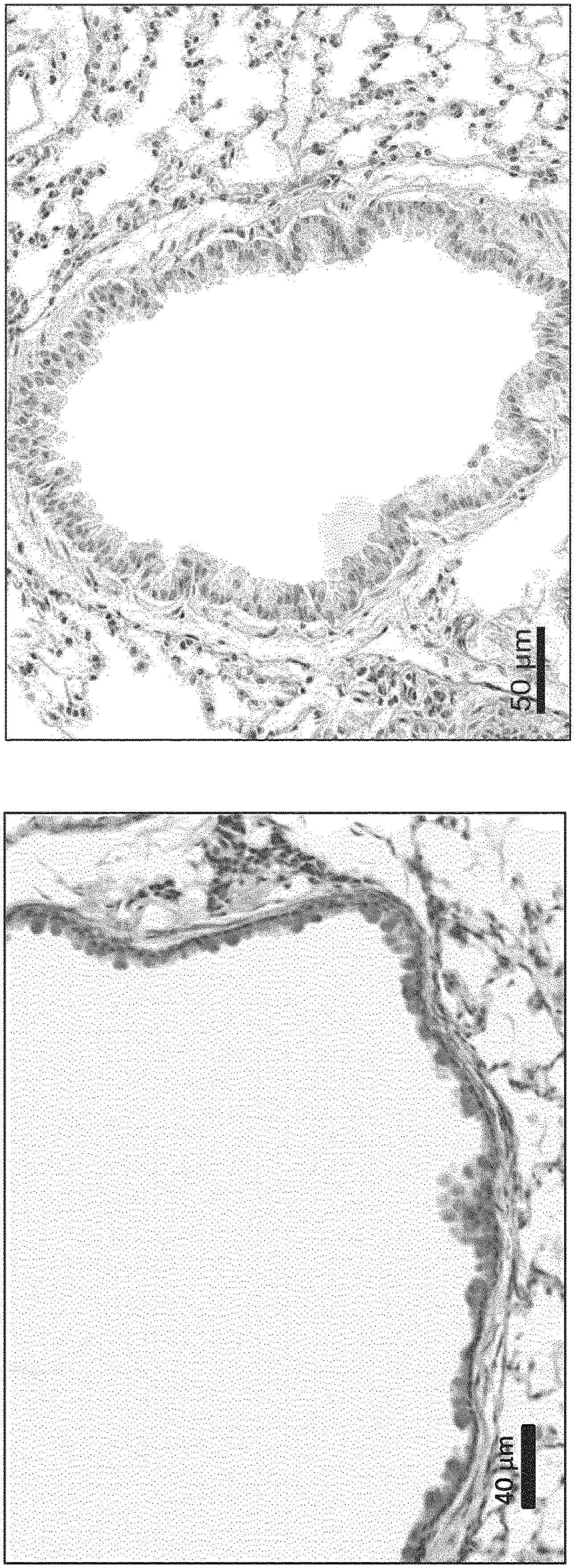

FIG. 20: Benzbromarone reduces mucus production.

A) Airway epithelial specific TMEM16A knockout mice accumulate mucus in club cells.

B) Benzbromarone treatment (1 mg/kg, intraperitoneally for 5 days) largely reduced mucus production in benzbromarone-treated mice with an airway epithelial specific TMEM16A knockout.

EXAMPLES

Example 1: TMEM16A Mouse Model

Knockout of TMEM16A in mouse airways was achieved by crossbreeding Vil1-Cre-TMEM16A$^{flox/flox}$ mice with FOXJ1-Cre transgenic mice. All animal experiments complied with the ARRIVE guidelines and were carried out in accordance with the U.K. Animals Act, 1986 and associated guidelines, EU Directive 2010/63/EU for animal experiments. All animal experiments were approved by the local ethics committee of the Government of Unterfranken/Würzburg (AZ: 55.2-2532-2-328) and were conducted according to the guidelines of the American Physiologic Society and the German law for the welfare of animals.

Intestinal sections were collected for histological analyses. Mouse airways were fixed by transcardial fixation and were embedded in paraffin or were used as cryosections. For paraffin sections, tissues were fixed in 4% paraformaldehyde (PFA), 0.2% picric acid and 3.4% sucrose in PBS, and were washed in methanol before embedding in paraffin. Sections were stained according to standard Periodic acid-Schiff (PAS) or Alcian Blue methods and assessed by light microscopy.

Enhanced pause (Penh) was measured in unrestrained animals by barometric plethysmography using a whole body plethysmograph.

Example 2: Inhibition of Basal Airway Mucus Secretion in the Absence of TMEM16A Mouse models were performed according to the previous example. For investigating mucus, IL-8 release, and leukocytes, tissues were fixed using 4% paraformaldehyde (PFA), 0.2% picric acid and 3.4% sucrose in PBS and washed in methanol before embedding in paraffin. Mucus was analyzed using standard Periodic acid-Schiff (PAS) or alcian blue staining. MUC5AC was stained using anti-MUC5AC mouse antibody (1:200, Abcam, ab3649) and a secondary antibody conjugated with Alexa 488 (Life Technologies, A-21206). Nuclei were stained with Hoe33342 (0.1 μg/ml PBS, Aplichem, Darmstadt, Germany). Quantikine ELISA kits (R&D systems) were used to measure secretion of the cytokine IL-8 by Calu3 cells.

For measuring mucociliary transport ex vivo, tracheas were removed, fixed with insect needles onto extra thick blot paper (Bio-Rad, Germany) and transferred into a chamber with water-saturated atmosphere at 37° C. Transport was measured by preparing tracheas as for Ussing chamber recordings. Tracheas isolated from mice were mounted with insect needles onto extra thick blot paper (Bio-Rad) and transferred into a water-saturated chamber at 37° C. The filter paper was perfused with Ringer solution at a rate of 1 ml/min and at 37° C. Polystyrene black-dyed microspheres were washed with Ringer solution and 10 1 of particle solution with 0.5% latex were added onto the mucosal surface of the trachea. Particle transport on different conditions was visualized by images every 10 s for 15 min using a Zeiss stereo microscope Discovery version 12, with digital camera AxioCam ICc1 and AxioVision software (Zeiss, Germany). Particle speed was calculated using AxioVision software (release 4.6.3, Zeiss).

Airways lacking epithelial cell specific expression of TMEM16A demonstrated an impressive accumulation of mucus, which was not due to an increased fraction of nonciliated club (Clara) cells (FIG. 3A-C; FIG. 9A). Accordingly, mucus accumulation was not due to an increased number of Clara cells or an increased number of goblet cells, but due to enhanced mucus load of the existing Clara cells. TMEM16A−/− airways did not show signs of inflammation, as no infiltration by CD45 positive leukocytes was detected. Moreover, analysis of airway cross-sections did not provide evidence for airway constriction (FIG. 3E). No mucus was found in the lumen of TMEM16A−/− airways. Basal mucociliary particle transport measured in isolated TMEM16A−/− tracheas was enhanced, but not further stimulated by ATP (FIG. 3F). Accordingly, basal mucus secretion is defective in the absence of TMEM16A.

Notably, the phenotype of TMEM16A−/− airways was strikingly similar to that found in Munc2−/− knockout mice, which have a defect in basal mucus secretion. Furthermore, TMEM16A−/− airways showed protruded club cells that accumulated secretory granules in the apical pole. Both the number of granules per cell and their size were enhanced (FIG. 9B,C).

TMEM16A knockout mice showed accumulated mucus within cells due to defective mucus secretion by mucus-producing epithelial cells of the airways. Thus, TMEM16A plays an essential role in mucus secretion, and inhibiting TMEM16A signaling allows for inhibiting mucus secretion.

Figure 1:
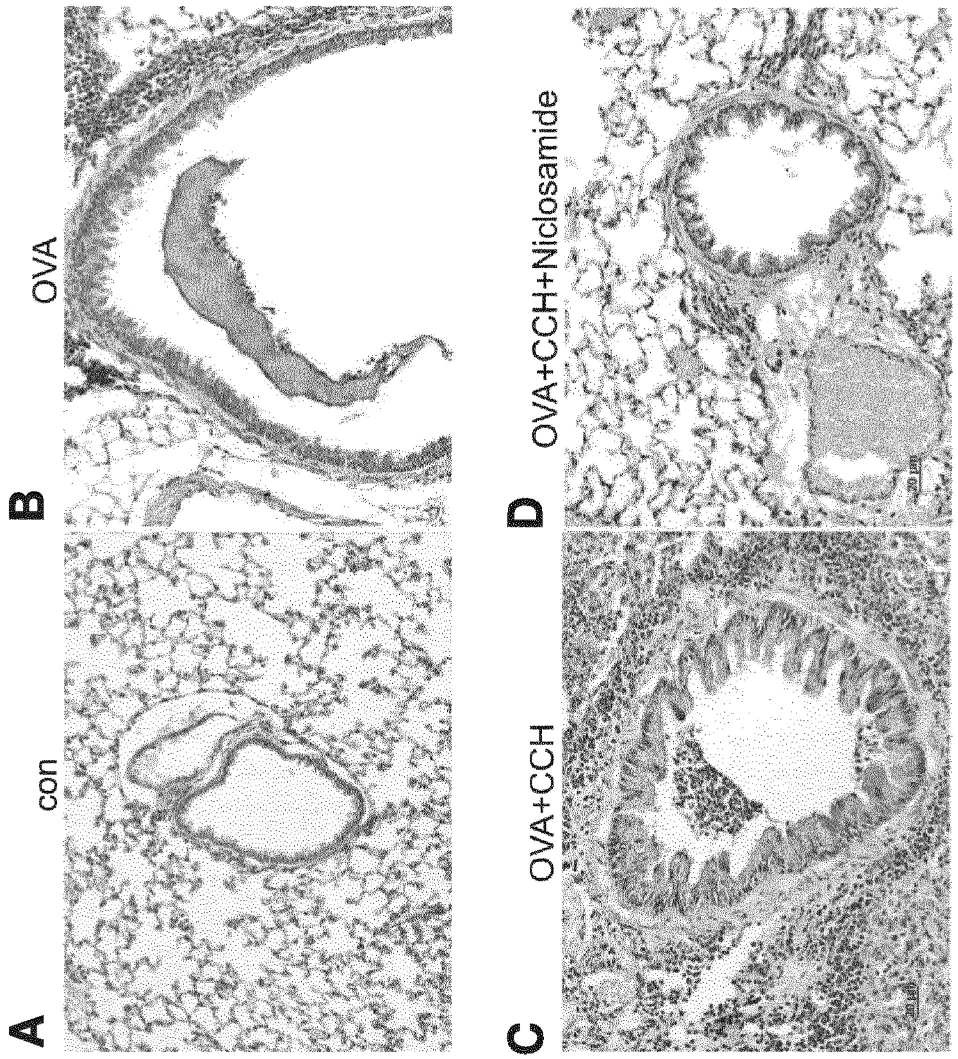
FIG. 1: Effect of niclosamide on mucus accumulation and inflammatory infiltration.

Example 3: ATP-Dependent but not Cholinergic Mucus Secretion is Compromised in TMEM16A−/− Airways All methods were performed as described in the previous examples. Mice were treated with ovalbumin (OVA) to induce an allergic reaction which leads to airway inflammation. Airways in control animals, i.e. without OVA-allergization, do not show excessive mucus and are relaxed. After allergization with OVA and development of airway inflammation, excessive mucus production and inflammatory infiltration with immune cells is observed. Activation of cholinergic receptors using the muscarinic agonist carbachol (CCH) results in constriction of the airways and secretion of mucus (FIG. 5A-C). 3-day treatment using niclosamide reduced the CCH-induced constriction of the airways (FIG. 1). Furthermore, mucus secretion and inflammatory infiltrates were reduced.

When exposed to ovalbumin, Th2-dependent goblet cell metaplasia and accumulation of mucus was observed in both TMEM16+/+ and TMEM16−/− airways, suggesting that TMEM16A is not essential for mucus production (FIG. 4A). In TMEM16A+/+ airways, pronounced mucus secretion was induced by nebulized ATP, but was significantly reduced in TMEM16A−/− mice (FIG. 4A,B). Accumulation of CD45 positive leucocytes in lungs of OVA-treated TMEM16A−/− animals was strongly reduced, suggesting attenuated airway inflammation in the absence of TMEM16A (FIG. 4C). In contrast to ATP (FIG. 4A,B), cholinergic stimulation of mucus secretion by nebulized carbachol was uncompromised in OVA-sensitized TMEM16A−/− mice (FIG. 5A,B).

Cholinergic airway constriction when measured as airway cross-section and enhanced pause (Phen) was not different in TMEM16A−/− mice (FIG. 5C,D). Accordingly, ATP but not cholinergic mucus secretion requires TMEM16A signalling.

Example 4: Basal and ATP-Dependent Intestinal Mucus Release, but not Cholinergic Goblet Cell Secretion, Require TMEM16A−/−

All methods were carried out as specified in the previous examples. Accumulation of mucus in both large and small intestinal goblet cells is observed in mice with intestinal epithelial specific knockout of TMEM16A (FIG. 6). In goblet cells from TMEM16A−/− mice, the mucus content per cell was enhanced, but not the number goblet cells per crypt (FIG. 6). Mucus covering the intestinal epithelium appeared thinner and more irregular in TMEM16A−/− mice. Muc2 expression was not upregulated in TMEM16A−/− intestine (FIG. 10B). Mucus accumulation in TMEM16A−/− intestine suggests defective basal mucus secretion.

Cholinergic stimulation released mucus from freshly isolated TMEM16A+/+ and TMEM16A−/− intestine (FIG. 6D-F). Mucus release was examined in more detail by perfusing freshly excised colon and collecting released mucus in vitro. For in vitro perfusion of intestines, mice were sacrificed and excised intestines were placed immediately in ice-cold Ringer solution and carefully flushed to remove residual luminal contents. The intestinal segments were mounted and perfused vertically in a custom-designed perfusion chamber with a constant temperature.

Due to compromised basal secretion, mucus accumulated in goblet cells of TMEM16A−/− colon, which was nearly completely released upon cholinergic (MCh) stimulation (FIG. 7C). Thus MCh-induced mucus release was much larger in the colon of TMEM16A−/− mice compared to TMEM16A+/+ mice. Stimulation with luminal ATP also released mucus in TMEM16A+/+ colon. Thus, the present invention discloses purinergic mucus release in naïve colon. In contrast to TMEM16A+/+ colon, no mucus was released by ATP in TMEM16A−/− colon (FIG. 7C). Thus basal and ATP-mediated mucus release in both airways and intestine are TMEM16A-dependent.

Example 5: TMEM16A Controls Intracellular $Ca^{2+}$ Signals and Membrane Exocytosis All methods were carried out as specified in the previous examples. For the measurements of $Ca^{2+}$, crypts were isolated from inverted proximal mouse colons using $Ca^{2+}$-free Ringer solution with 1 mM DTT and 1 μM indomethacin for 20 min at 37° C. Crypts were loaded with 10 μM Fura2-AM (Biotum, USA) and 1 mg/ml BSA (Sigma-Aldrich) in ringer solution for 1 h at RT. Intracellular $Ca^{2+}$ was measured by loading crypts with 2 mM Fura-2/AM and 0.02% Pluronic F-127 (Life Technologies, Germany) in ringer solution for 1 h at room temperature. Fluorescence was detected in cells perfused with Ringer's solution at 37° C. using an inverted microscope (Axiovert S100, Zeiss, Germany) and a high-speed polychromator system (VisiChrome, Germany). Fura-2 was excited at 340/380 nm, and emission was recorded between 470 and 550 nm using a CoolSnap camera (CoolSnap HQ, Visitron).

TMEM16A controls ATP-induced compartmentalized $Ca^{2+}$ signals by enhancing $Ca^{2+}$ store release and store operated $Ca^{2+}$ influx (SOCE). The present invention discloses that intestinal mucus release by ATP requires luminal $Ca^{2+}$ which is, however, not needed for MCh-induced secretion. Intracellular $Ca^{2+}$ increase stimulated by ATP was much reduced in goblet cells of freshly isolated TMEM16A−/− crypts, while $Ca^{2+}$ increase induced by basolateral cholinergic stimulation was only slightly compromised in the absence of TMEM16A (FIG. 11). Because apical intracellular $Ca^{2+}$ prepares granules via the $Ca^{2+}$ sensors Munc13 and Doc2B for release by the exocytic machinery, TMEM16A may be necessary for exocytosis. TMEM16A-expressing HEK293 cells were examined showing an enhanced membrane capacitance. Membrane capacitance is proportional to membrane surface and was found to be larger in the absence and presence of the $Ca^{2+}$ ionophore ionomycin (FIG. 8). Enhanced expression of the membrane surface marker CD8 was found in the presence of TMEM16A.

The present invention discloses that TMEM16A controls exocytosis of mucus-filled granules by providing $Ca^{2+}$ to an apical signaling compartment. Increase of intracellular $Ca^{2+}$ leads to fusion of mucin-filled granules with the apical membrane. TMEM16A is thus indispensable for basal and ATP-controlled mucus secretion in airways and intestine. A compound for use according to the present invention is efficient in treating a disease characterized by dysregulated mucus secretion and/or production by inhibiting basal and/or ATP-controlled mucus secretion via TMEM16A signaling. A compound for use according to the present invention is also efficient in treating said disease by bronchodilation.

Example 6: Niflumic Acid (NFA) is an Inhibitor of TMEM16 and Blocks Airway Mucus OVA-induced allergic airway inflammation in mice caused pronounced airway goblet cell metaplasia. Exposure of inflammatory lungs to aerosolized carbachol (CCH) induced massive release of mucus as well as airway contraction (FIG. 14A-C). Pretreatment of sensitized animals for three days by tracheal instillation of the $Cl^-$ channel blocker niflumic acid (NFA), abolished airway mucus and completely blocked CCH-induced airway contraction, when measuring airway cross sections. NFA is a well know inhibitor of Ca2+ activated $Cl^-$ channels and inhibits TMEM16A. The two main TMEM16 paralogs expressed in airway epithelial and smooth muscle cells, TMEM16A and TMEM16F, were expressed in HEK293 cells and the whole cell currents upon activation by the $Ca^{2+}$ ionophore ionomycin (Iono) were measured. Large whole cell currents were activated by simulation of TMEM16A and TMEM16F with Iono, and current activation was potently suppressed by NFA (FIG. 14D-F). The data suggest TMEM16A/F being in charge of both mucus production and contraction of airway smooth muscle (ASM). Novel therapeutic strategies for the treatment of inflammatory airway diseases such as CF may therefore consider the use of inhibitors of TMEM16.

Example 7: Niclosamide and Derivatives: Potent Inhibitors of Anoctamins and Ca2+ Signaling Using patch clamp experiments, the present inventors demonstrate the inhibitory effect of niclosamide on TMEM16A outward currents activated by purinergic stimulation of HEK293 cells (FIG. 15A-C). Similar to TMEM16A, also overexpressed TMEM16F was inhibited by niclosamide (FIG. 15D). The effect of niclosamide was also examined on endogenous TMEM16A expressed in HT29 colonic carcinoma cells, which were stably transfected with iodide-sensitive yellow fluorescent protein (YFP). TMEM16A was activated by ionomycin and TMEM16A currents were measured as iodide quenching. Niclosamide and the related compounds niclosamide-ETHO, tizoxanide, and nitazoxanide inhibited endogenous TMEM16A in the low nanomolar range, and were more potent than the well-known inhibitors CaCCinhAO1 or dichlorophen (FIG. 15E).

Example 8: Niclosamide Inhibits Mucus Secretion, ASM Contraction, and Inflammation OVA-induced mucus production was strongly reduced by both NFA and niclosamide (FIG. 16A,B). The present inventors disclose that airway epithelial knockout of TMEM16A causes a defect in basal, i.e. ATP-mediated mucus secretion. This resulted in an accumulation of mucus under control (non-inflammatory) conditions. Mucus synthesis under inflammatory (OVA) conditions and mucus release upon cholinergic stimulation, however, were not compromised (FIG. 16C). In both wt and TMEM16A−/− airways, application of niclosamide for three days before applying CCH, strongly reduced mucus synthesis, so that very little mucus was left over to be secreted by CCH (FIG. 16C-E). Because basal mucus production still occurs in the absence of TMEM16A, other TMEM16 paralogs may also be in charge of mucus synthesis. The expression of the three main TMEM16 paralogs in isolated airway epithelial cells was analyzed, and it was found that TMEM16A, also TMEM16F and TMEM16K, were upregulated through Th2 driven goblet cell metaplasia and mucus hyperproduction after OVA—sensitization (FIG. 16F).

Attenuation of airway inflammation by niclosamide suggests inhibition of inflammatory mediators. Calu3 airway epithelial cells were exposed to LPS for 48 hrs and the release of the neutrophil attractor interleukin 8 (IL-8) was measured. IL-8 release was enhanced by LPS-exposure and the release was clearly inhibited in the presence of niclosamide. Upon stimulation with the Th2 cytokine IL-13, Calu3 cells produced MUC5AC. IL-13 induced synthesis of Muc5AC was clearly inhibited when TMEM16F-expression was knocked down by siRNA. As observed for mouse airways, incubation with niclosamide also largely reduced Muc5AC-expression in Calu3 human airway epithelial cells. Niclosamide did not change expression of either TMEM16A or TMEM16F. Taken together, airway epithelial knockout of TMEM16A caused a defect in mucus secretion, while mucus production was retained (FIG. 16C). Niclosamide is a potent inhibitor of both TMEM16A and TMEM16F, inhibits mucus production but does not affect expression of TMEM16A/F. Accordingly, TMEM16F is relevant for mucus production.

Example 9: Airway Epithelial Knockout of TMEM16F Attenuates Mucus Production and Secretion Mice with an airway epithelial knockout of TMEM16F (FoxJ1-Cre-TMEM16F$^{flox/flox}$) were generated to examine further the role of TMEM16F for mucus production and mucus release in mouse. Alcian blue staining indicated accumulation of mucus in airways of FoxJ1-Cre-TMEM16F$^{flox/flox}$ mice, which was not observed in littermate controls. This suggests a role of TMEM16F for basal mucus secretion in mouse airways, similar to TMEM16A. OVA-sensitization induced pronounced goblet cell metaplasia and mucus production in control mice, which however, was attenuated in the FoxJ1-Cre-TMEM16F$^{flox/flox}$ mice. Acute muscarinic stimulation with aerosolized CCH released mucus from airway epithelia of FoxJ1-Cre-TMEM16F$^{flox/flox}$ and control mice. The data suggest a role of TMEM16F for basal mucus release similar to that of TMEM16A, and a role of TMEM16F for mucus production.

Example 10: TMEM16F is Required for Intestinal Mucus Production and Secretion

It was examined whether TMEM16F is also important for intestinal mucus secretion and acute mucus release was measured in freshly excised colonic segments mounted in a vertical custom-designed perfusion chamber at 37° C. and 24 mmol/1 $HCO_3^-$/5% CO2. Secretion of mucus was induced by basolateral perfusion with methacholine (MCh) and by luminal perfusion of ATP. Both, MCh- and ATP-induced secretion of mucus in normal wt colon (TMEM16F$^{flox/flox}$) as well as colon lacking epithelial expression of TMEM16F (Vil1-Cre-TMEM16F$^{flox/flox}$) (FIG. 17A).

In contrast to Vil1-Cre-TMEM16A$^{flox/flox}$ colon, a defect in ATP-driven mucus secretion was not detected in Vil1-Cre-TMEM16F$^{flox/flox}$ intestine, but MCh-induced secretion was lightly enhanced. This indicates a defect in basal secretion, leading to accumulation of mucus, which is then released by MCh-stimulation. Compared to Vil1-Cre-MEM16A$^{flox/flox}$ intestine (which has a defect in mucus release but not mucus production), MCh-induced mucus release was reduced in Vil1-Cre-TMEM16F$^{flox/flox}$. Therefore, mucus production appears compromised in the absence of TMEM16F. Vil1-Cre-TMEM16F$^{flox/flox}$ mice showed normal expression of purinergic or muscarinic receptors (data not shown). Mucus was stained before and after induction of secretion by MCh or ATP. In Vil1-Cre-MEM16F$^{flox/flox}$ intestine, basal mucus staining was enhanced, and release was attenuated after stimulation with ATP (but not MCh), similar to Vil1-Cre-TMEM16A$^{flox/flox}$ mice (FIG. 17B-E). Thus, TMEM16F is required for purinergic but not cholinergic mucus secretion in airways and intestine.

Example 11: Niclosamide Blocks Mucus Secretion and Inhibits Intestinal $Ca^{2+}$ Signals It was examined whether niclosamide inhibits intestinal mucus secretion. To this end, niclosamide was added to the perfusate. This clearly inhibited mucus secretion activated by luminal ATP but not basolateral MCh (FIG. 18A). Niclosamide was applied in vivo by intraperitoneal (ip) injection, or was applied orally by gavage three days before intestinal perfusion. Both ip and oral application of niclosamide completely inhibited ATP-induced release of mucus. Although mucus release was inhibited by niclosamide, it did not accumulate in goblet cells, indicating inhibition of mucus production (FIG. 18B-E). TMEM16F plays a crucial role for intracellular $Ca^{2+}$ signaling. The present inventors detected reduced $Ca^{2+}$ increase upon ATP-stimulation of freshly isolated crypt cells from Vil1-Cre-TMEM16F$^{flox/flox}$ mice. In contrast, CCH-induced $Ca^{2+}$ rise was not affected. It shows that TMEM16F is relevant for purinergic (luminal) but not cholinergic (basolateral) receptor signaling. ATP-induced $Ca^{2+}$ rise was potently inhibited by low concentrations of niclosamide. Comparable results were obtained in cells from large intestine. Increase in FM4-64 fluorescence in the plasma membrane is a marker for membrane exocytosis. The present inventors detected that ATP-stimulation (but not cholinergic stimulation) of HEK293 cells expressing TMEM16F induced FM4-64 fluorescence, i.e. exocytosis. Conclusively, the present inventors disclose that both airway and intestinal mucus production and secretion depends on TMEM16F, and is potently inhibited by niclosamide.

Example 12: Niclosamide Reduces Intestinal Mucus Load

Additional experiments were performed that fully support the above findings indicating that inhibitors of TMEM16 proteins block mucus production and mucus secretion. FIG. 19 demonstrates mucus staining by alcian blue in jejunum from mice homozygous for the cystic fibrosis mutation CFTRdeltaF508/deltaF508. Animals were treated for 7 days and subsequently sacrificed. Jejunum was excised, fixed in Carnoy Solution and embedded in paraffin. Sham treated mice (intraperitoneal injection of corn oil for 7 days) demonstrate significant amounts of mucus in the intestinal lumen (FIG. 19A). Untreated animals showed comparable mucus load (not shown). In contrast, animals injected intraperitoneally for 7 days with niclosamide (13 mg/kg/day, dissolved in corn oil) demonstrate smaller jejunal diameters and largely reduced mucus (FIG. 19B). Treatment by niclosamide was well tolerated by the animals. The data therefore demonstrate that treatment with niclosamide reduces intestinal mucus load, thus having a beneficial effect in the treatment of CF.

Example 13: Benzbromarone Reduces Mucus Production

In another set of experiments, airway epithelial specific TMEM16A knockout mice were treated with benzbromarone. Airway epithelial specific TMEM16A knockout mice accumulate mucus in club cells, likely due to a secretory defect (FIG. 20A).

Benzbromarone (1 mg/kg, intraperitoneally) was applied for 5 days to mice with an airway epithelial specific knockout of TMEM16A. Benzbromarone treatment largely reduced mucus production in benzbromarone-treated mice (FIG. 20B), indicating that mucus production is independent of TMEM16A and that benzbromarone potently inhibits mucus production. Thus benzbromarone is beneficial in the treatment of CF by reducing airway mucus plugging and therefore improving lung function.

REFERENCES

[1] Huang F, Zhang H, Wu M, Yang H, Kudo M, Peters C J, et al. Calcium-activated chloride channel TMEM16A modulates mucin secretion and airway smooth muscle contraction. Proc. Natl. Acad. Sci U.S.A (2012); 109: 16354-9.

[2] Lin J, Jiang Y, Li L, Liu Y, Tang H, et al. TMEM16A mediates the hypersecretion of mucus induced by Interleukin-13. Exp Cell Res (2015); 260-269.

3. Miner K, Liu B, Wang P, Labitzke K, Gaida K, et al. The antihelminthic niclosamide is a potent TMEM16A antagonist that fully bronchodilates airways. BioRxiv (2018); DOI: 10.1101/254888.

The features of the present invention disclosed in the specification, the claims, and/or in the accompanying figures may, both separately and in any combination thereof, be material for realizing the invention in various forms thereof.

The invention claimed is:

1. A method of treating a disease in a patient, wherein said disease is cystic fibrosis, and wherein said disease is characterized by dysregulated release of proinflammatory cytokines by any of airway epithelial goblet cells, club cells, and ciliated epithelial cells, said method comprising administering a compound to said patient, wherein said compound is an inhibitor of a TMEM16 protein and wherein said compound is benzbromarone, or a pharmaceutically acceptable salt thereof, or wherein said compound is selected from 5-chloro-N-(2-chloro-4-nitrophenyl)-2-hydroxybenzamide, also referred to as niclosamide, and 2-aminoethanol 5-chloro-N-(2-chloro-4-nitrophenyl)-2-hydroxybenzamide, also referred to as clonitralid or niclosamide ethanolamine salt, and wherein said method involves inhibiting dysregulated release of interleukin-8 (IL-8) in any of airway epithelial goblet cells, club cells, and ciliated epithelial cells.

2. The method according to claim 1, wherein said disease is further characterized by dysregulated basal mucus secretion and/or dysregulated mucus production.

3. The method according to claim 1, wherein said method involves inhibiting basal mucus secretion and/or mucus production and/or dysregulated release of proinflammatory cytokines in any of airway epithelial goblet cells, club cells, and ciliated epithelial cells.

4. The method according to claim 1, wherein said TMEM16 protein is selected from TMEM16A, TMEM16B, TMEM16C, TMEM16D, TMEM16E, TMEM16F, TMEM16G, TMEM16H, TMEM16J, and TMEM16K.

5. The method according to claim 1, wherein said disease affects the respiratory tract and/or the gastrointestinal tract.

6. The method according to claim 1, wherein said compound is administered orally, nasally, mucosally, intrabronchially, intrapulmonarily, intradermally, subcutaneously, intravenously, intramuscularly, intravascularly, intrathecally, intraocularly, intraarticularly, or intranodally.

7. The method according to claim 1, wherein said TMEM16 is selected from TMEM16A and TMEM16F.

* * * * *